(12) United States Patent
Blumberg et al.

(10) Patent No.: US 11,225,490 B2
(45) Date of Patent: *Jan. 18, 2022

(54) PRODRUGS OF SECONDARY AMINE COMPOUNDS

(71) Applicant: Alkermes Pharma Ireland Limited, Dublin (IE)

(72) Inventors: Laura Cook Blumberg, Lincoln, MA (US); John A. Lowe, III, Stonington, CT (US); Orn Almarsson, Shrewsbury, MA (US); Juan C. Alvarez, Lincoln, MA (US); Tarek A. Zeidan, Lexington, MA (US)

(73) Assignee: Alkermes Pharma Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/562,698

(22) Filed: Sep. 6, 2019

(65) Prior Publication Data

US 2020/0087317 A1 Mar. 19, 2020

Related U.S. Application Data

(60) Division of application No. 14/612,853, filed on Feb. 3, 2015, now Pat. No. 10,954,250, which is a continuation of application No. 13/714,830, filed on Dec. 14, 2012, now Pat. No. 8,969,337.

(60) Provisional application No. 61/576,244, filed on Dec. 15, 2011.

(51) Int. Cl.
   *C07D 495/04* (2006.01)
   *A61K 47/54* (2017.01)
(52) U.S. Cl.
   CPC .......... *C07D 495/04* (2013.01); *A61K 47/542* (2017.08)
(58) Field of Classification Search
   CPC .................................................. C07D 495/04
   See application file for complete search history.

(56) References Cited

U.S. PATENT DOCUMENTS

| 4,916,230 A | 4/1990 | Alexander |
| 6,169,084 B1 | 1/2001 | Bunnell et al. |
| 2002/0028806 A1 | 3/2002 | Goebel et al. |
| 2004/0151753 A1 | 8/2004 | Chen et al. |

FOREIGN PATENT DOCUMENTS

| JP | 57-21400 | | 2/1982 |
| JP | 08-217787 | | 8/1996 |
| WO | WO1996/018605 A1 | | 6/1996 |
| WO | WO199618605 | * | 6/1996 |
| WO | WO1999/049857 A1 | | 10/1999 |
| WO | WO2001/054481 A2 | | 8/2001 |
| WO | WO2001/056358 A2 | | 8/2001 |
| WO | WO2003/095454 A1 | | 11/2003 |
| WO | WO2005/009944 A1 | | 2/2005 |
| WO | WO2005/028473 A1 | | 3/2005 |
| WO | WO2007/087416 A2 | | 8/2007 |
| WO | WO2011/163594 A2 | | 12/2011 |
| WO | 2013016668 A2 | | 1/2013 |
| WO | WO2013/008182 A1 | | 1/2013 |
| WO | WO2013/017974 A1 | | 2/2013 |

OTHER PUBLICATIONS

Lund et al. Exp. Opin. Pharmacother. (2000), vol. 1, pp. 305-323. (Year: 2000).*
Lippard, et al., "The Art of Chemistry", Nature, vol. 416, 2002.
Siegel, S. J. et al., "Extended Release Drug Delivery Strategies in Psychiatry: Theory to Practice", Psychiatry (2005); Jun. 2005, 22-31.
Simplicio, et al., "Prodrugs for Amines", Molecules, vol. 13, 2008, 519-547.

* cited by examiner

*Primary Examiner* — Taina D Matos Negron
(74) *Attorney, Agent, or Firm* — Elmore Patent Law Group, P.C.; Carolyn Elmore; Joseph Zucchero

(57) ABSTRACT

The present invention relates to compounds of Formula I:

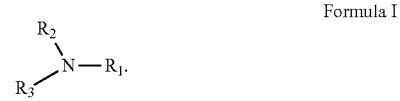

Formula I

15 Claims, 4 Drawing Sheets

PRODRUGS OF SECONDARY AMINE COMPOUNDS

RELATED APPLICATIONS

Figure 1:
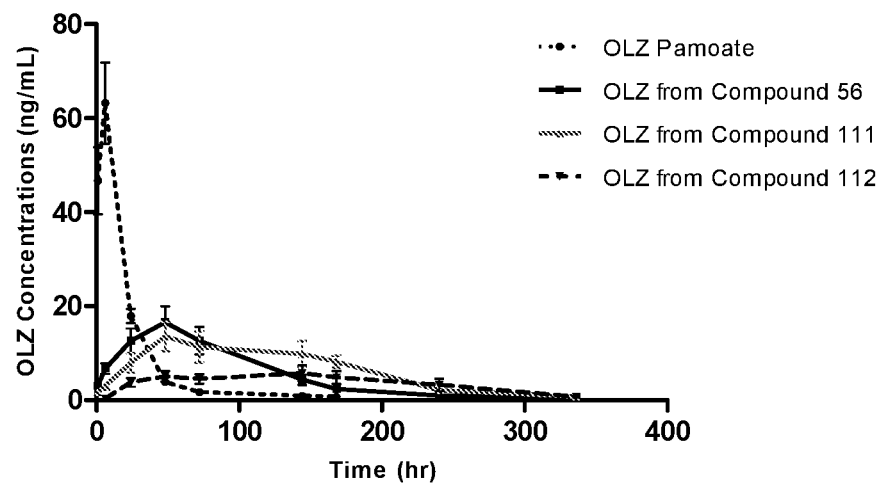

This application is a divisional of U.S. application Ser. No. 14/612,853, filed on Feb. 3, 2015, which is a continuation of U.S. application Ser. No. 13/714,830, filed on Dec. 14, 2012, now U.S. Pat. No. 8,969,337, issued Mar. 3, 2015 which claims the benefit of U.S. Provisional Application No. 61/576,244, filed on Dec. 15, 2011.

The entire teachings of the above applications are incorporated herein by reference.

BACKGROUND OF THE INVENTION

(i) Field of the Invention

The present invention relates to prodrugs of secondary amine compounds.

(ii) Background of the Invention

Drug delivery systems are often critical for the safe effective administration of a biologically active agent. Perhaps the importance of these systems is best realized when patient compliance and consistent dosing are taken into consideration. For instance, reducing the dosing requirement for a drug from four-times-a-day to a single dose per day would have significant value in terms of ensuring patient compliance and optimizing therapy.

Optimization of a drug's bioavailability has many potential benefits. For patient convenience and enhanced compliance it is generally recognized that less frequent dosing is desirable. By extending the period through which the drug is released, a longer duration of action per dose is expected. This will then lead to an overall improvement of dosing parameters such as taking a drug once a day where it has previously required four times a day dosing or once a week or even less frequently when daily dosing was previously required. Many drugs are presently given at a once a day dosing frequency. Yet, not all of these drugs have pharmacokinetic properties that are suitable for dosing intervals of exactly twenty-four hours. Extending the period through which these drugs are released would also be beneficial.

One of the fundamental considerations in drug therapy involves the relationship between blood levels and therapeutic activity. For most drugs, it is of primary importance that serum levels remain between a minimally effective concentration and a potentially toxic level. In pharmacokinetic terms, the peaks and troughs of a drug's blood levels ideally fit well within the therapeutic window of serum concentrations. For certain therapeutic agents, this window is so narrow that dosage formulation becomes critical.

In an attempt to address the need for improved bioavailability, several drug release modulation technologies have been developed. Enteric coatings have been used as a protector of pharmaceuticals in the stomach and microencapsulating active agents using protenoid microspheres, liposomes or polysaccharides has been effective in abating enzyme degradation of the active agent. Enzyme inhibiting adjuvants have also been used to prevent enzymatic degradation.

A wide range of pharmaceutical formulations provide sustained release through microencapsulation of the active agent in amides of dicarboxylic acids, modified amino acids or thermally condensed amino acids. Slow release rendering additives can also be intermixed with a large array of active agents in tablet formulations.

While microencapsulation and enteric coating technologies impart enhanced stability and time-release properties to active agent substances these technologies suffer from several shortcomings. Incorporation of the active agent is often dependent on diffusion into the microencapsulating matrix, which may not be quantitative and may complicate dosage reproducibility. In addition, encapsulated drugs rely on diffusion out of the matrix or degradation of the matrix, or both, which is highly dependent on the chemical properties and water solubility of the active agent. Conversely, water-soluble microspheres swell by an infinite degree and, unfortunately, may release the active agent in bursts with limited active agent available for sustained release. Furthermore, in some technologies, control of the degradation process required for active agent release is unreliable. For example, an enterically coated active agent depends on pH to release the active agent and, due to variability in pH and residence time, it is difficult to control the rate of release.

Several implantable drug delivery systems have utilized polypeptide attachment to drugs. Additionally, other large polymeric carriers incorporating drugs into their matrices are used as implants for the gradual release of drug. Yet another technology combines the advantages of covalent drug attachment with liposome formation where the active ingredient is attached to highly ordered lipid films.

Thus, there is a need for an active agent delivery system that poses a reduced potential risk to the patient, is able to deliver certain active agents that have been heretofore not formulated (or are difficult to formulate in a sustained release formulation) for release over a sustained period of time, and which is convenient for patient dosing.

There is a generally recognized need for sustained delivery of drugs that can reduce the dosing requirement and allows for controlled and sustained release of the parent drug, and also avoids irregularities of release and cumbersome formulations encountered with typical dissolution controlled sustained release methods.

SUMMARY OF THE INVENTION

The present invention provides an alternative approach to prodrugs for secondary amine and related compounds which results in reduced risks to the patient. The invention also extends the period during which a secondary amine parent drug, or related compound, is released and absorbed after administration to the patient and provides a longer duration of action per dose than is currently expected. In one embodiment, the compounds suitable for use in the methods of the invention are labile prodrugs of secondary amine parent drugs that are derivatized through carbamate-linked prodrug moieties that reduce the solubility and polarity of the prodrug compound as compared to the parent drug. The carbamate linked esters are expected to get cleaved by esterases in vivo, releasing the chemically unstable intermediate which then releases the aldehyde linker and carbon dioxide.

In one embodiment, the invention provides compounds represented by Formula I:

Formula I wherein:
R$_1$ is —C(O)OC(R$_4$)(R$_5$)—OC(O)(G$_{12}$)$_m$R$_6$;
  wherein each R$_4$ and R$_5$ is independently selected from hydrogen, C$_1$-C$_3$ alkyl, aryl or substituted aryl; preferably, hydrogen or methyl;
  G$_{12}$ is selected from absent, NH, CH$_2$, —S— or —O—;
  m is 0 or 1;
  R$_6$ is selected from C$_{13}$-C$_{26}$-alkyl, substituted C$_{13}$-C$_{26}$-alkyl, C$_{13}$-C$_{26}$-alkenyl, substituted C$_{13}$-C$_{26}$-alkenyl, C$_3$-C$_{26}$-alkynyl, substituted C$_3$-C$_{26}$-alkynyl, C$_3$-C$_{26}$-cycloalkyl, and substituted C$_3$-C$_{26}$-cycloalkyl, aryl-C$_{13}$-C$_{26}$-alkyl, substituted aryl-C$_{13}$-C$_{26}$-alkyl, C$_1$-C$_{10}$-aryl, substituted C$_1$-C$_{10}$-aryl, heteroaryl-C$_{13}$-C$_{26}$-alkyl, substituted heteroaryl-C$_{13}$-C$_{26}$-alkyl; optionally substituted C$_{13}$-C$_{26}$-alkylaryl, optionally substituted C$_{13}$-C$_{26}$-alkenylaryl and optionally substituted C$_{13}$-C$_{26}$-alkynylaryl;
R$_2$ and R$_3$, together with the nitrogen atom to which they are attached, form a secondary amine-containing parent drug, or a substituted secondary amine-containing parent drug.

In a preferred embodiment, the invention relates to a prodrug of Formula I wherein upon administration to the patient, release of the parent drug from the prodrug is sustained release.

In another embodiment, the invention relates to pharmaceutical compositions comprising a compound of Formula I, a pharmaceutically acceptable carrier, and methods of using a compound of Formula I in therapy.

In a further embodiment, the prodrug compounds of the invention are formulated with a biocompatible sustained release delivery system for delivery of the prodrug wherein the system is preferably capable of minimizing accelerated hydrolytic cleavage of the prodrug by minimizing exposure of the prodrug to water. Preferred delivery systems include biocompatible polymeric matrix delivery systems capable of minimizing the diffusion of water into the matrix having the prodrug dispersed therein.

In another embodiment, the invention provides a method of sustained delivery of a secondary amine-containing parent drug comprising administering to a subject an effective amount of a prodrug compound produced by substituting a labile, hydrophobic carbamate-linked prodrug moiety (represented by —R$_1$) on the secondary amine nitrogen atom of the parent drug. Preferably the prodrug compound has decreased solubility under physiological conditions and sustained activity upon dosing compared to the parent drug compound. In one embodiment, the secondary amine-containing parent drug is represented by Formula II:

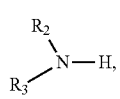

Formula II wherein R$_2$ and R$_3$ are as previously defined. In this embodiment the prodrug is represented by Formula I:

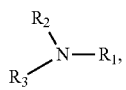

Formula I wherein R$_1$, R$_2$ and R$_3$ are as previously defined.

The invention also provides a method of administering a secondary amine-containing parent drug comprising administering to a subject an effective amount of a prodrug compound (Formula I) produced by substituting a labile, hydrophobic carbamate-linked prodrug moiety (—R$_1$) on the secondary amine nitrogen atom. The method substantially eliminates undesirable side effects seen upon administration of the parent drug itself by lowering the maximum plasma concentration of the parent drug while maintaining sustained therapeutic levels. In certain embodiments, the side effect of the parent drug is sedation. In a preferred embodiment, the prodrug compound is a compound of Formula I and the parent drug is a compound of Formula II.

In another embodiment, the invention provides a method of producing a prodrug of a parent secondary amine-containing drug compound, wherein the prodrug has decreased solubility under physiological conditions and sustained activity upon dosing compared to the parent drug compound. The method comprises modifying the parent drug by substituting a labile, hydrophobic prodrug moiety on the secondary amine nitrogen atom. Preferably, the parent drug compound is represented by Formula II, the labile moiety is represented by Ri, where R$_1$ is as defined above, and the prodrug is represented by Formula I.

The invention also provides pharmaceutical compositions comprising a compound of Formula I and methods of using a compound of Formula I in therapy.

FIGURES

FIG. 1: Mean plasma olanzapine concentration after intramuscular injection of Compound-56, 111, and 112 to rats.

Figure 2:
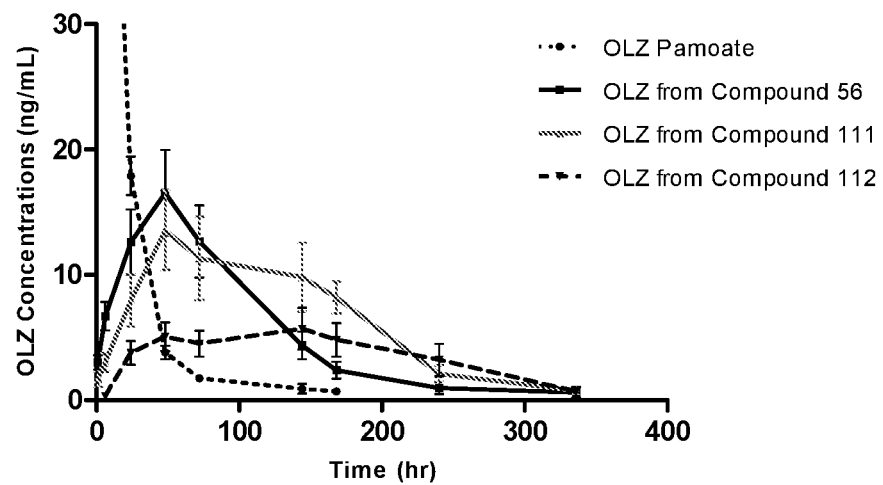

FIG. 2: Expanded view of mean plasma olanzapine concentration after intramuscular injection of Compound-56, 111, and 112 to rats.

Figure 3:
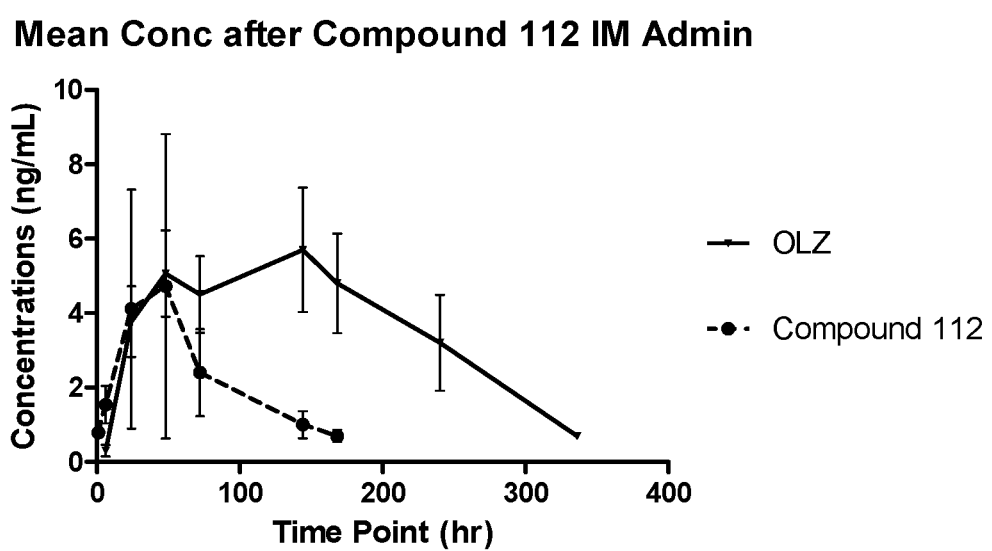

FIG. 3: Plasma concentrations of olanzapine and Compound-112 after intramuscular administration of Compound-112.

Figure 4:
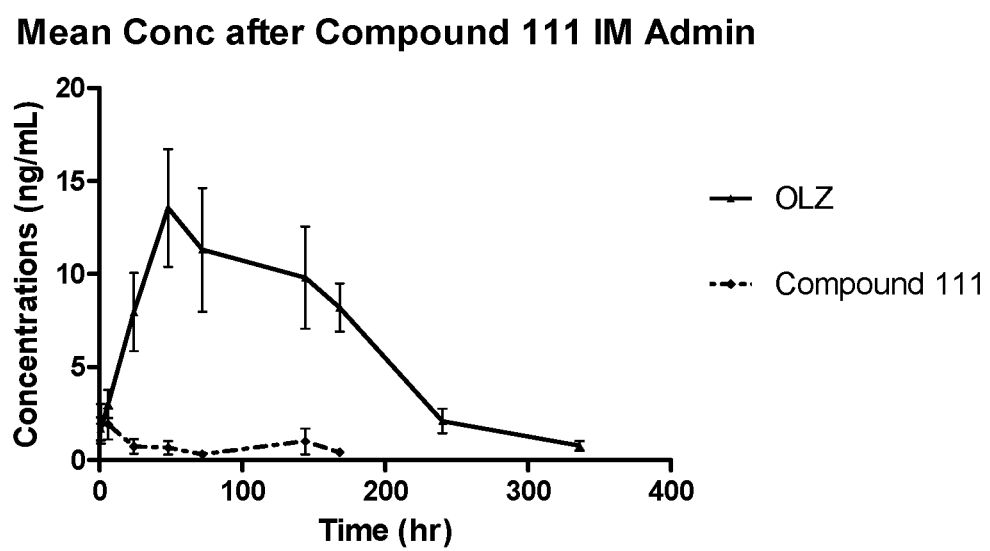

FIG. 4: Plasma concentrations of olanzapine and Compound-111 after intramuscular administration of Compound-111.

DETAILED DESCRIPTION OF THE INVENTION

The prodrug compounds of the present invention having the general structure of Formula I provide sustained or extended release to the parent drug, where the parent drug is produced by the enzymatic or hydrolytic cleavage of the labile R$_1$ group:

Formula I wherein:
R$_1$ is —C(O)OC(R$_4$)(R$_5$)—OC(O)(G$_{12}$)$_m$R$_6$;
  wherein each R$_4$ and R$_5$ is independently selected from hydrogen, C$_1$-C$_3$ alkyl, aryl or substituted aryl; preferably, hydrogen or methyl;
  G$_{12}$ is selected from absent, NH, CH$_2$, —S— or —O—;
  m is 0 or 1;
  R$_6$ is selected from C$_{13}$-C$_{26}$-alkyl, substituted C$_{13}$-C$_{26}$-alkyl, C$_{13}$-C$_{26}$-alkenyl, substituted C$_{13}$-C$_{26}$-alkenyl, $C_3$-$C_{26}$-alkynyl, substituted $C_3$-$C_{26}$-alkynyl, $C_3$-$C_{26}$-cycloalkyl, and substituted $C_3$-$C_{26}$-cycloalkyl, aryl-$C_{13}$-$C_{26}$-alkyl, substituted aryl-$C_{13}$-$C_{26}$-alkyl, $C_1$-$C_{10}$-aryl, substituted $C_1$-$C_{10}$-aryl, heteroaryl-$C_{13}$-$C_{26}$-alkyl, substituted heteroaryl-$C_{13}$-$C_{26}$-alkyl; optionally substituted $C_{13}$-$C_{26}$-alkylaryl, optionally substituted $C_{13}$-$C_{26}$-alkenylaryl and optionally substituted $C_{13}$-$C_{26}$-alkynylaryl;

$R_2$ and $R_3$, together with the nitrogen atom to which they are attached, form a secondary amine-containing parent drug, or a substituted secondary amine-containing parent drug.

In a preferred embodiment, the invention relates to a prodrug of Formula I wherein upon administration to the patient, release of the parent drug from the prodrug is sustained release.

In one embodiment, the secondary amine-containing parent drug is represented by Formula II:

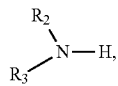

Formula II wherein $R_2$ and $R_3$ are as previously defined. In this embodiment the prodrug is represented by Formula I:

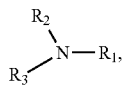

Formula I wherein $R_1$, $R_2$ and $R_3$ are as previously defined.

In one embodiment, $R_6$ is an optionally substituted $C_{13}$-$C_{26}$-aliphatic, $C_{13}$-$C_{26}$-aromatic, or $C_{13}$-$C_{26}$-alkoxy (carbonate) group that reduces the solubility of the prodrug under physiological conditions compared to the parent drug.

In one embodiment, both $R_4$ and $R_5$ are hydrogen. In another embodiment, $R_5$ is hydrogen and $R_4$ is methyl. In yet a third embodiment, both $R_4$ and $R_5$ are methyl.

In one embodiment, the invention provides compounds of Formula I in which $R_1$ is selected from —C(O)OCH($R_4$)—OC(O)$R_6$, —C(O)OCH($R_4$)—OC(O)O$R_6$, —C(O)OCH($R_4$)—OC(O)N($R_6$)$R_7$, and —C(O)OCH($R_4$)—OC(O)NH$R_6$, where $R_4$, $R_5$, and $R_6$, are as previously defined; $R_7$ is selected from hydrogen, alkyl, substituted alkyl, aryl, substituted aryl, aliphatic and substituted aliphatic.

In one embodiment, $R_6$ or $R_7$ is optionally substituted $C_{13}$-$C_{26}$-alkyl, $C_{13}$-$C_{26}$-alkenyl, or $C_{13}$-$C_{26}$-alkynyl. In a preferred embodiment, $R_6$ is optionally substituted $C_{15}$-$C_{24}$-alkyl, $C_{15}$-$C_{24}$-alkenyl, or $C_{15}$-$C_{24}$-alkynyl. In a more preferred embodiment, $R_6$ or $R_7$ is optionally substituted $C_{17}$-$C_{22}$-alkyl, $C_{17}$-$C_{22}$-alkenyl, or $C_{17}$-$C_{22}$-alkynyl. In a more preferred embodiment, $R_6$ is optionally substituted $C_{19}$-alkyl, $C_{19}$-alkenyl, or $C_{19}$-alkynyl. In a more preferred embodiment, $R_6$ is optionally substituted $C_{17}$-alkyl, $C_{17}$-alkenyl, or $C_{17}$-alkynyl.

In one embodiment, $R_6$ or $R_7$ is a $C_{13}$-$C_{26}$- or $C_{13}$-$C_{26}$-alkyl, -alkenyl or -alkynyl group, corresponding to one of formulas (i)-(v) below.

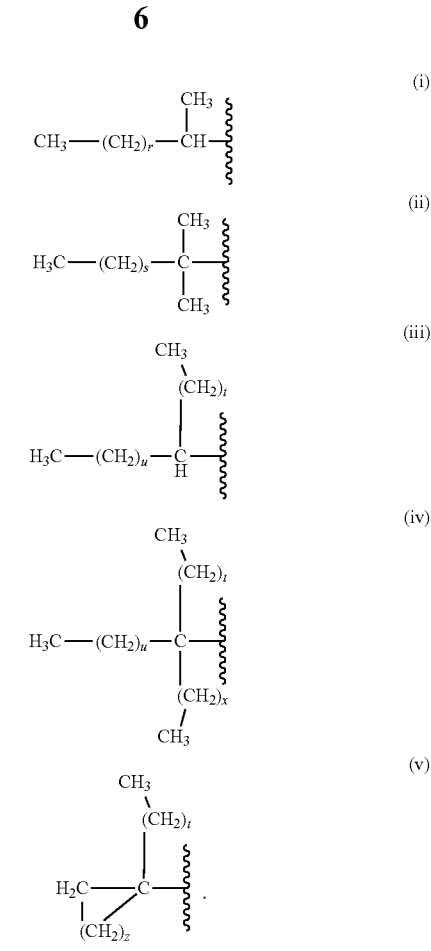

In these groups, r is an integer selected from 11 to 24, and s is an integer selected from 11 to 24. Each of t and u is independently an integer selected from 1 to 24, provided that the sum of t and u is from 12 to 34. Each of v, w and x is independently an integer selected from 1 to 24, provided that the sum of v, w and x is from 13 to 44. z is an integer selected from 1 to 10 and y is an integer selected from 11 to 24. Preferably, r is an integer selected from 15 to 17; s is an integer selected from 15 to 17; the sum of t and u is selected from 16 to 26; the sum of v, w and x is selected from 17 to 35; and the sum of y and z is selected from 16 to 23. $R_6$ can also be an alkenyl or alkynyl group derived from one of the alkyl groups of formulas (i) to (v), by replacement of one or more carbon-carbon single bonds with a carbon-carbon double bond or a carbon-carbon triple bond.

In another embodiment, $R_6$ or $R_7$ is an optionally substituted (3-branched $C_{13}$-$C_{26}$-alkyl, $C_{13}$-$C_{26}$-alkenyl or $C_{13}$-$C_{26}$-alkynyl, preferably optionally substituted β-branched $C_{17}$-$C_{22}$-alkyl, $C_{17}$-$C_{22}$-alkenyl or $C_{17}$-$C_{22}$-alkynyl. Suitable examples of β-branched alkyl groups include 2-methyl-$C_{13}$-$C_{26}$-alkyl and 2,2-dimethyl-$C_{13}$-$C_{26}$-alkyl, including 2-methylpropyl; 2,2-dimethylpropyl; 2-methylbutyl; 2,2-dimethylbutyl; 2-methylpentyl; 2,2-dimethylpentyl; and 2-ethyl-2-methylbutyl.

The secondary amine-containing parent drug can be any secondary amine-containing parent drug that induces a desired local or systemic effect. Such parent drugs include broad classes of compounds. Several examples include: respiratory drugs, including antiasthmatic agents; analgesic agents; antidepressants; antianginal agents; antiarrhythmic agents; antihypertensive agents; antidiabetic agents; antihistamines; anti-infective agents such as antibiotics; antiinflammatory agents; antiparkinsonism drugs; antipsychotics; antipyretic agents; antiulcer agents; attention deficit hyperactivity disorder (ADHD) drugs; central nervous system stimulants; cough and cold preparations, including decongestants; and psychostimulants.

Examples of secondary-amine containing parent drugs from which prodrugs of the invention may be derived include: alprenolol, acebutolol, amidephrine, amineptine, amosulalol, amoxapine, amphetaminil, atenolol, atomoxetine, balofloxacin, bamethan, befunolol, benazepril, benfluorex, benzoctamine, betahistine, betaxolol, bevantolol, bifemelane, bisoprolol, brinzolamide, bufeniode, butethamine, camylofine, carazolol, carticaine, carvedilol, cephaeline, ciprofloxacin, clozapine, clobenzorex, clorprenaline, cyclopentamine, delapril, demexiptiline, denopamine, desipramine, desloratadine (clarinex), diclofenac, dimetofrine, dioxadrol, dobutamine, dopexamine, doripenem, dorzolamide, droprenilamine, duloxetine, eltoprazine, enalapril, enoxacin, epinephrine, ertapenem, esaprazole, esmolol, etoxadrol, fasudil, fendiline, fenethylline, fenfluramine, fenoldopam, fenoterol, fenproporex, flecainide, fluoxetine, formoterol, frovatriptan, gaboxadol, garenoxacin, gatifloxacin, grepafloxacin, hexoprenaline, imidapril, indalpine, indecainide, indeloxazine hydrochloride, isoxsuprine, ispronicline, labetalol, landiolol, lapatinib, levophacetoperane, lisinopril, lomefloxacin, lotrafiban, maprotiline, mecamylamine, mefloquine, mepindolol, meropenem, metapramine, metaproterenol, methoxyphenamine, dtmp (dextrorotary methylphenidate), methylphenidate, metipranolol, metoprolol, mitoxantrone, mivazerol, moexipril, moprolol, moxifloxacin, nebivolol, nifenalol, nipradilol, norfloxacin, nortriptyline, nylidrin, olanzapine, oxamniquine, oxprenolol, oxyfedrine, paroxetine, perhexiline, phenmetrazine, phenylephrine, phenylpropylmethylamine, pholedrine, picilorex, pimefylline, pindolol, pipemidic acid, piridocaine, practolol, pradofloxacin, pramipexole, pramiverin, prenalterol, prenylamine, prilocaine, procaterol, pronethalol, propafenone, propranolol, propylhexedrine, protokylol, protriptyline, pseudoephedrine, reboxetine, rasagiline, (r)-rasagiline, repinotan, reproterol, rimiterol, ritodrine, safinamide, salbutamol/albuterol, salmeterol, sarizotan, sertraline, silodosin, sotalol, soterenol, sparfloxacin, spirapril, sulfinalol, synephrine, tamsulosin, tebanicline, tianeptine, tirofiban, tretoquinol, trimetazidine, troxipide, varenicline (champix), vildagliptin, viloxazine, viquidil and xamoterol.

Preferred secondary amine-containing parent drugs from which prodrugs of the invention are derived include atenolol, atomoxetine, clozapine, desipramine, desloratadine (clarinex), diclofenac, doripenem, duloxetine, enalapril, ertapenem, fluoxetine, metoprolol, mecamylamine, meropenem, methylphenidate, dtmp (dextrorotary methylphenidate), olanzapine, paroxetine, pramipexole, rasagiline, (r)-rasagiline, salbutamol/albuterol, tamsulosin, varenicline (chantix), and vildagliptin. In a more preferred embodiment, the secondary amine-containing parent drug is selected from clozapine, duloxetine, mecamylamine, pramipexole, rasagiline, (r)-rasagiline, and olanzapine.

In a preferred embodiment, a compound of the invention provides sustained delivery of the parent drug over hours, days, weeks or months when administered parenterally to a subject. For example, the compounds can provide sustained delivery of the parent drug for up to 7, 15, 30, 60, 75 or 90 days or longer. Without being bound by theory, it is believed that the compounds of the invention form an insoluble depot upon parenteral administration, for example subcutaneous, intramuscular or intraperitoneal injection.

The present invention is intended to encompass any parent drug compound or any substituted parent drug compound which contains a secondary amine group and which is biologically active and can be derivatized according to the present invention to afford the corresponding compounds of formula I. While the secondary amine-containing parent drugs from which the prodrugs of the invention may be derived are numerous, many of the chemical structures of the prodrugs of the invention can be characterized by certain general structure types. One type includes those wherein the secondary amine nitrogen is part of a cyclic (including bicyclic or tricyclic) aliphatic group such as piperidine, piperazine, morpholine, pyrrolidine, azapine, and diazapine. Another type includes those wherein the secondary amine nitrogen is a linear amine within an aliphatic chain, or as a diaryl amine or an aromatic amine.

Examples of secondary amine-containing parent drugs, and the functional secondary amine group which provides the site of attachment of the carbamate-linked prodrug moiety, are provided in the section below. Unless otherwise stated, the structural formula of a compound herein is intend to represent all enantiomers, racemates and diastereomers of that compound.

Prodrugs of Atenolol

Atenolol is a known beta adrenergic blocker that is used in the treatment of hypertension, angina, and arrhythmia. Its chemical name is 2-(4-{2-hydroxy-3-[(propan-2-yl)amino]propoxy}phenyl)acetamide. In one embodiment, the invention relates to a prodrug of atenolol having the following structure:

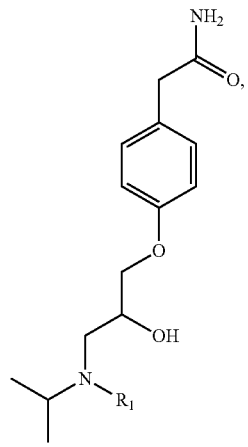

wherein $R_1$ is as defined above; preferably $R_1$ is selected from the structures of Tables 1-3.

Prodrugs of Atomoxetine

Atomoxetine is used in the treatment of attention-deficit hyperactivity disorder (ADHD). Its chemical name is (−)-M-methyl-γ-(2-methylphenoxy)benzenepropanamine. In one embodiment, the invention relates to a prodrug of atomoxetine having the following structure:

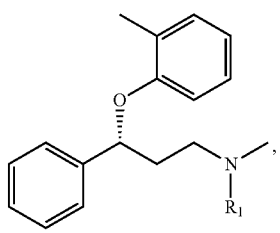

wherein $R_1$ is as defined above; preferably $R_1$ is selected from the structures of Tables 1-3.

Prodrugs of Desipramine

Desipramine is used in the treatment of depression. Its chemical name is 3-(10,11-dihydro-5H-dibenzo[b,f]azepin-5-yl)-N-methylpropan-l-amine. In one embodiment, the invention relates to a prodrug of desipramine having the following structure:

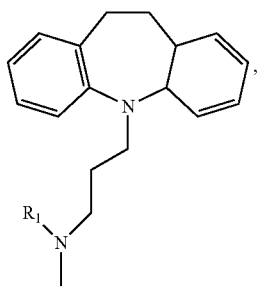

wherein $R_1$ is as defined above; preferably $R_1$ is selected from the structures of Tables 1-3.

Prodrugs of Diclofenac

Diclofenac is a non-steroidal anti-inflammatory agent (NSAID with antipyretic and analgesic actions. Its chemical name is 2-{2-[(2,6-dichlorophenyl)amino]phenyl}acetic acid. In one embodiment, the invention relates to a prodrug of diclofenac having the following structure:

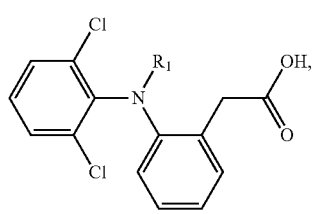

wherein $R_1$ is as defined above; preferably $R_1$ is selected from the structures of Tables 1-3.

Prodrugs of Duloxetine

Duloxetine is a known selective serotonin-norepinephrine reuptake inhibitor (selective SNRI) that is used in the treatment of depression and anxiety. Its chemical name is methyl[(3S)-3-(naphthalen-1-yloxy)-3-(thiophen-2-yl)propyl]amine. In one embodiment, the invention relates to a prodrug of duloxetine having the following structure:

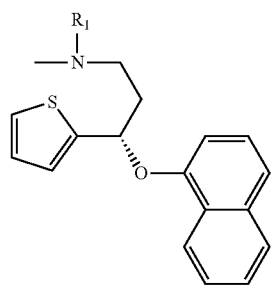

wherein $R_1$ is as defined above; preferably $R_1$ is selected from the structures of Tables 1-3.

Prodrugs of Enalapril

Enalapril is a known angiotensin-converting enzyme (ACE) inhibitor that is used in the treatment of hypertension. Its chemical name is (2S)-1-[(2S)-2-{[(2S)-1-ethoxy-1-oxo-4-phenylbutan-2-yl]amino}propanoyl]pyrrolidine-2-carboxylic acid. In one embodiment, the invention relates to a prodrug of enalapril having the following structure:

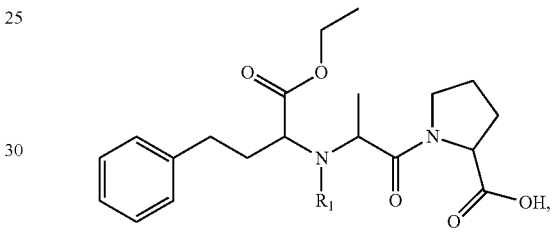

wherein $R_1$ is as defined above; preferably $R_1$ is selected from the structures of Tables 1-3.

Prodrugs of Fluoxetine

Fluoxetine is a known highly specific serotonin uptake inhibitor that is used in the treatment of depression. Its chemical name is methyl({3-phenyl-3-[4-(trifluoromethyl)phenoxy]propyl})amine. In one embodiment, the invention relates to a prodrug of fluoxetine having the following structure:

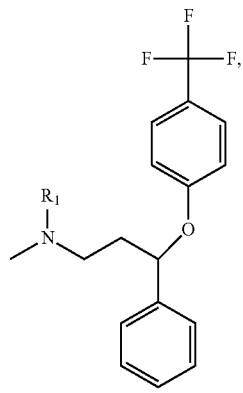

wherein $R_1$ is as defined above; preferably $R_1$ is selected from the structures of Tables 1-3.

Prodrugs of Metoprolol

Metoprolol is a known cardioselective β1-adrenergic blocking agent used in the treatment of acute myocardial infarction (MI), heart failure, angina pectoris and mild to moderate hypertension. Its chemical name is {2-hydroxy-3-[4-(2-methoxyethyl)phenoxy]propyl}(propan-2-yl)amine.
In one embodiment, the invention relates to a prodrug of metoprolol having the following structure:

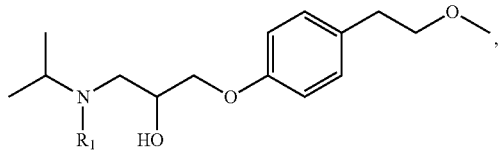

wherein $R_1$ is as defined above; preferably $R_1$ is selected from the structures of Tables 1-3.

Prodrugs of Mecamylamine

Mecamylamine is a known nicotinic antagonist used in the treatment of smoking addiction and depression. Its chemical name is N,2,3,3-tetramethylbicyclo[2.2.1]heptan-2-amine. In one embodiment, the invention relates to a prodrug of mecamylamine having the following structure:

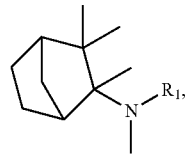

wherein $R_1$ is as defined above; preferably $R_1$ is selected from the structures of Tables 1-3.

Prodrugs of Pramipexole

Pramipexole is a known non-ergoline dopamine agonist used in the treatment of Parkinson's disease and restless legs syndrome (RLS). Its chemical name is (6R)-6-N-propyl-4,5,6,7-tetrahydro-1,3-benzothiazole-2,6-diamine. In one embodiment, the invention relates to a prodrug of pramipexole having the following structure:

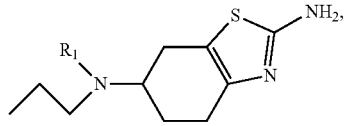

wherein $R_1$ is as defined above; preferably $R_1$ is selected from the structures of Tables 1-3.

Prodrugs of Rasagiline

Rasagiline is a known irreversible inhibitor of monoamine oxidase used in the treatment of Parkinson's disease. Its chemical name is (1R)-N-(prop-2-yn-1-yl)-2,3-dihydro-1H-inden-1-amine. In one embodiment, the invention relates to a prodrug of rasagiline having the following structure:

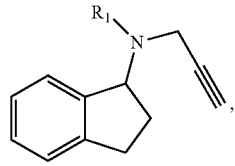

wherein $R_1$ is as defined above; preferably $R_1$ is selected from the structures of Tables 1-3.

(R)-Rasagiline (R)-Rasagiline is a known irreversible inhibitor of monoamine oxidase used in the treatment of Parkinson's disease. Its chemical name is (1R)-N-(prop-2-yn-1-yl)-2,3-dihydro-1H-inden-1-amine. In one embodiment, the invention relates to a prodrug of (R)-rasagiline having the following structure:

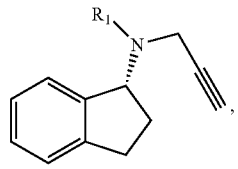

wherein $R_1$ is as defined above; preferably $R_1$ is selected from the structures of Tables 1-3.

Prodrugs of Salbutamol

Salbutamol is a known short-acting, selective beta2-adrenergic receptor agonist used in the treatment of asthma and Chronic Obstructive Pulmonary Disease (COPD). The chemical name of salbutamol is 4-[2-(tert-butylamino)-1-hydroxyethyl]-2-(hydroxymethyl)phenol. In one embodiment, the invention relates to a prodrug of salbutamol having the following structure:

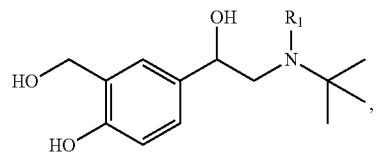

wherein $R_1$ is as defined above; preferably $R_1$ is selected from the structures of Tables 1-3.

Prodrugs of Tamsulosin

Tamsulosin is a known selective antagonist of alpha-1A and alpha-1B-adrenoceptors that is used in the treatment of hypertrophy of the prostate. Its chemical name is 5-[(2R)-2-{[2-(2-ethoxyphenoxy)ethyl]amino}propyl]-2-methoxy-benzene-1-sulfonamide. In one embodiment, the invention relates to a prodrug of tamsulosin having the following structure:

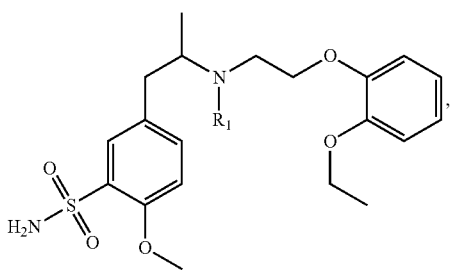

wherein $R_1$ is as defined above; preferably $R_1$ is selected from the structures of Tables 1-3.

Prodrugs of Vildagliptin

Vildagliptin is a known anti-hyperglycemic agent (antidiabetic drug) of the dipeptidyl peptidase-4 (DPP-4) inhibitor class of drugs that is used to inhibit the inactivation of glucagon-like peptide-1 (GLP-1) and glucose-dependent insulinotropic polypeptide (GIP) by DPP-4. Its chemical name is (2S)-1-{2-[(3-hydroxyadamantan-1-yl)amino]

acetyl}pyrrolidine-2-carbonitrile. In one embodiment, the invention relates to a prodrug of vildagliptin having the

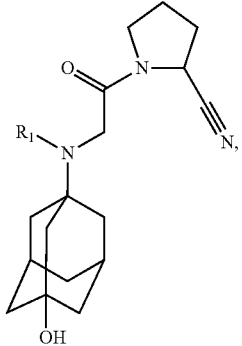

wherein $R_1$ is as defined above; preferably $R_1$ is selected from the structures of Tables 1-3.

Prodrug Chemistry Via Secondary Nitrogen of Azepine Moiety Prodrugs of Varenicline Varenicline is a known partial agonist of the alpha4/beta2 subtype of the nicotinic acetylcholine receptor that is used in the treatment of smoking addiction. Its chemical name is 7,8,9,10-tetrahydro- 6,10-methano-6H-pyrazino (2,3-h)(3) benzazepine. In one embodiment, the invention relates to a prodrug of varenicline having the following structure:

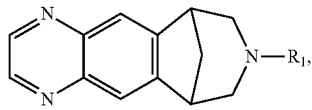

wherein $R_1$ is as defined above; preferably $R_1$ is selected from the structures of Tables 1-3.

Prodrug Chemistry Via Secondary Nitrogen of Diazepine Moiety Clozapine

Clozapine is a known atypical antipsychotic agent that used in the treatment of neurodisorders. Its chemical name is 8-chloro-11-(4-methylpiperazin-1-yl)-5H-dibenzo[b,e][1,4]diazepine. In one embodiment, the invention relates to a prodrug of clozapine having the following structure:

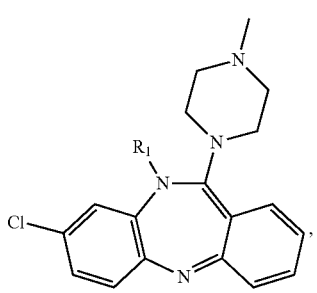

wherein $R_1$ is as defined above; preferably $R_1$ is selected from the structures of Tables 1-3.

In one embodiment, the invention relates to a prodrug of clozapine having the following structure:

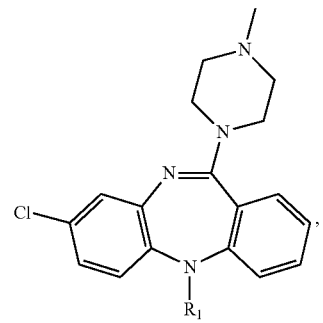

wherein $R_1$ is as defined above; preferably $R_1$ is selected from the structures of Tables 1-3.

Olanzapine

Olanzapine is a known atypical antipsychotic that is used in the treatment of schizophrenia and bipolar disorder as well as other neurodisorders. Its chemical name is 2-methyl-4-(4-methyl-1-piperazinyl)-10H-thieno[2,3 -b] [1,5]benzodiazepine. In one embodiment, the invention relates to a prodrug of olanzapine having the following structure:

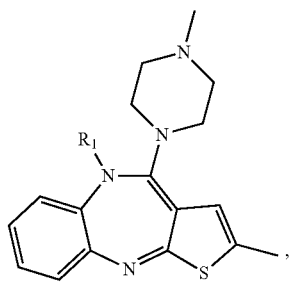

wherein $R_1$ is as defined above; preferably $R_1$ is selected from the structures of Tables 1-3.

In one embodiment, the invention relates to a prodrug of olanzapine having the following structure:

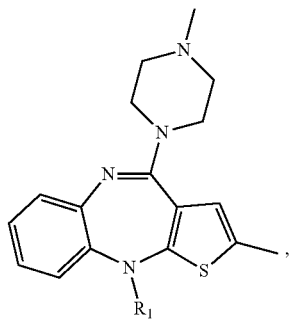

wherein $R_1$ is as defined above; preferably $R_1$ is selected from the structures of Tables 1-3.

Prodrug Chemistry Via Secondary Nitrogen of Piperidine Moiety Desloratadine

Desloratadine is a known H1-antagonist and is used as a non-sedating antihistamine. Its chemical name is 8-chloro-6,11-dihydro-11-(4-piperdinylidene)-5H-benzo[5,6]cyclohepta[1,2-b]pyridine. In one embodiment, the invention relates to a prodrug of desloratadine having the following structure:

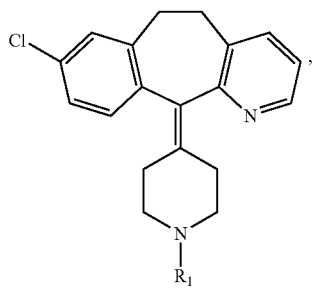

wherein $R_1$ is as defined above; preferably $R_1$ is selected from the structures of Tables 1-3.

Prodrugs of Methylphenidate

Methylphenidate is a known psychostimulant that is used in the treatment of attention deficit disorders and narcolepsy. Its chemical name is methyl 2-phenyl-2-(piperidin-2-yl) acetate. In one embodiment, the invention relates to a prodrug of methylphenidate having the following structure:

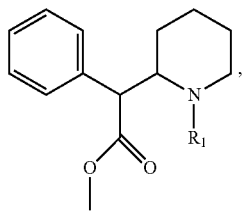

wherein $R_1$ is as defined above; preferably $R_1$ is selected from the structures of Tables 1-3.

Prodrugs of Dexmethylphenidate

Dexmethylphenidate is the dextrorotary form of methylphenidate. It is a norepinephrine-dopamine reuptake inhibitor (NDRI) and a psychostimulant, and is used for the treatment of Attention Deficit Hyperactivity Disorder (ADHD). Its chemical name is methyl (2R)-2-phenyl-2-[(2R)-piperidin-2-yl]acetate. In one embodiment, the invention relates to a prodrug of dexmethylphenidate having the following structure:

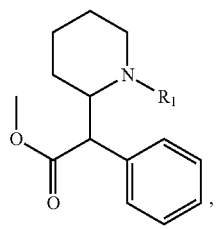

wherein $R_1$ is as defined above; preferably $R_1$ is selected from the structures of Tables 1-3.

Prodrugs of Paroxetine

Paroxetine is a known serotonin uptake inhibitor that is used in the treatment of depression. Its chemical name is (3S,4R)-3-[(2H-1,3-benzodioxol-5-yloxy)methyl]-4-(4-fluorophenyl)piperidine. In one embodiment, the invention relates to a prodrug of peroxetine having the following structure:

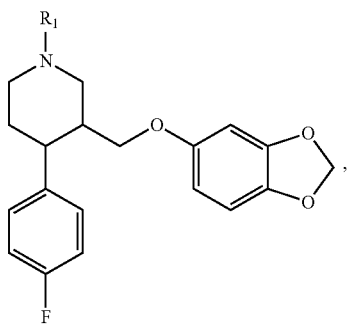

wherein $R_1$ is as defined above; preferably $R_1$ is selected from the structures of Tables 1-3.

Prodrug Chemistry Via Secondary Nitrogen of Pyrrolidine Moiety Doripenem

Doripenem is a known broad spectrum antibiotic that is used in the treatment of bacterial infections. Its chemical name is (4R,5S,6S)-6-(1-hydroxyethyl)-4-methyl-7-oxo-3-[(3S,5S)-5-[(sulfamoylamino)methyl]pyrrolidin-3-yl]sulfanyl-1-azabicyclo[3.2.0]hept-2-ene-2-carboxylic acid. In one embodiment, the invention relates to a prodrug of doripenem having the following structure:

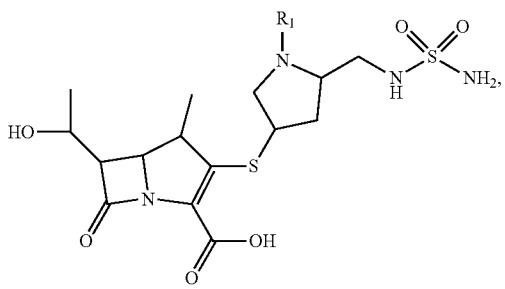

wherein $R_1$ is as defined above; preferably $R_1$ is selected from the structures of Tables 1-3.

Prodrugs of Ertapenem

Ertapenem is a known broad spectrum antibiotic that is used in the treatment of bacterial infections. Its chemical name is (4R,5S,6S)-3-{[(3S,5S)-5-[(3-carboxyphenyl)carbamoyl]pyrrolidin-3-yl]sulfanyl}-6-[(1R)-1-hydroxyethyl]-4-methyl-7-oxo-1-azabicyclo[3.2.0]hept-2-ene-2-carboxylic acid. In one embodiment, the invention relates to a prodrug of ertapenem having the following structure:

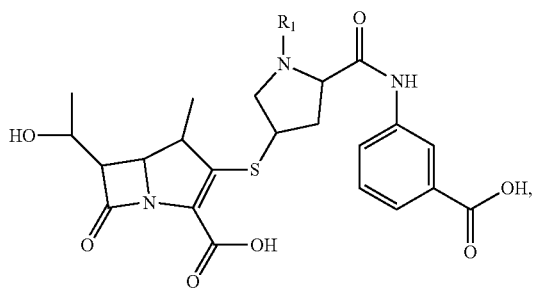

wherein $R_1$ is as defined above; preferably $R_1$ is selected from the structures of Tables 1-3.

Prodrugs of Meropenem

Meropenem is a known broad spectrum antibiotic that is used in the treatment of bacterial infections. Its chemical name is (4R,5S,6S)-3-{[(2S,5S)-5-(dimethylcarbamoyl)pyrrolidin-2-yl]sulfanyl}-6-[(1R)-1-hydroxyethyl]-4-methyl-7-oxo-1-azabicyclo[3.2.0]hept-2-ene-2-carboxylic acid. In one embodiment, the invention relates to a prodrug of meropenem having the following structure:

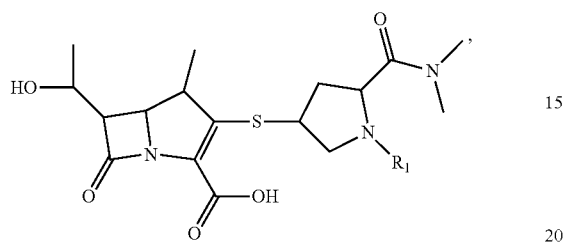

wherein $R_1$ is as defined above; preferably $R_1$ is selected from the structures of Tables 1-3.

In preferred embodiments, $R_1$ in formula I is selected from Tables 1-3.

TABLE 1

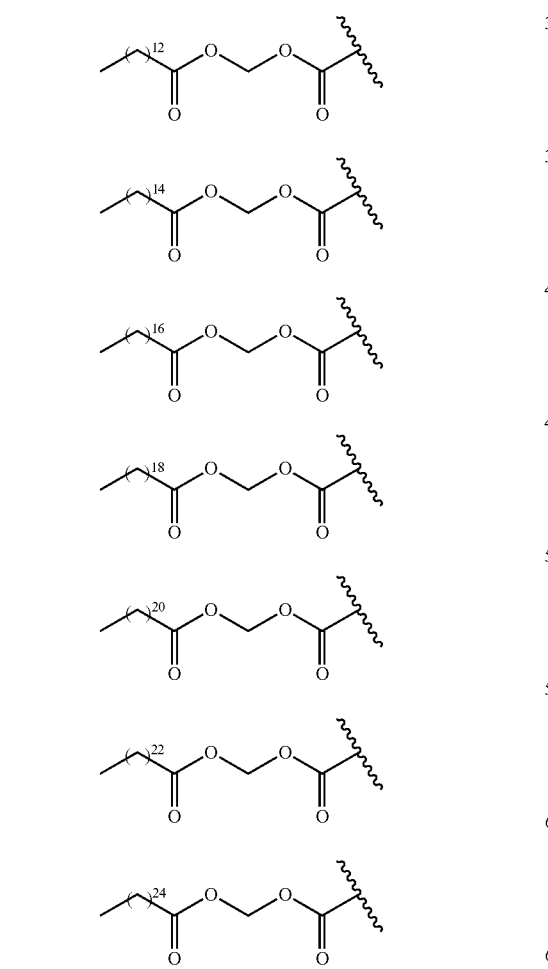

TABLE 1-continued

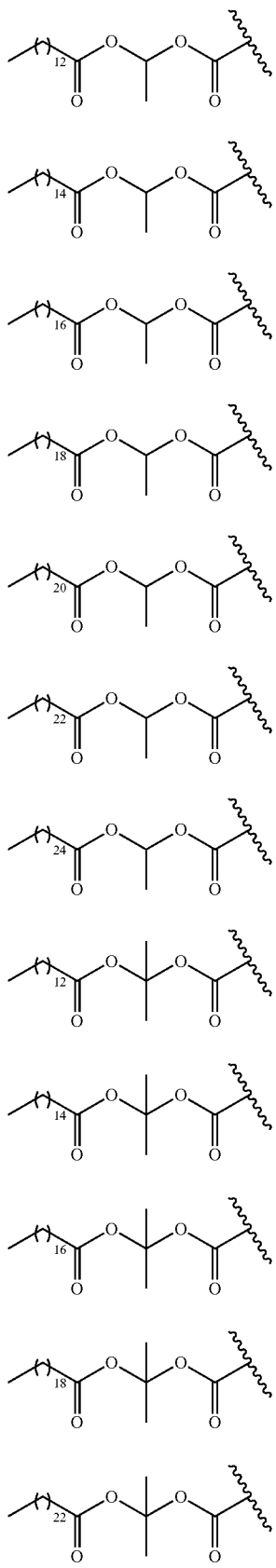

TABLE 1-continued
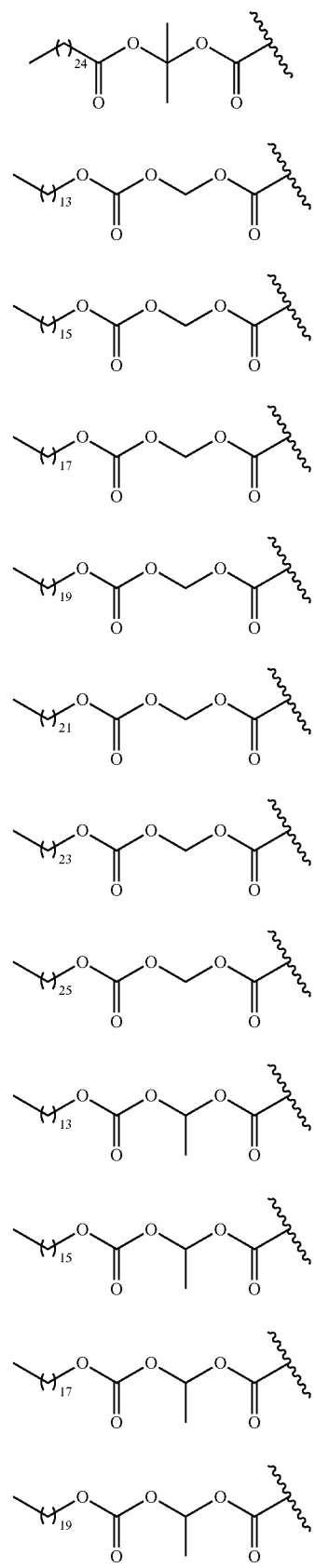
TABLE 1-continued
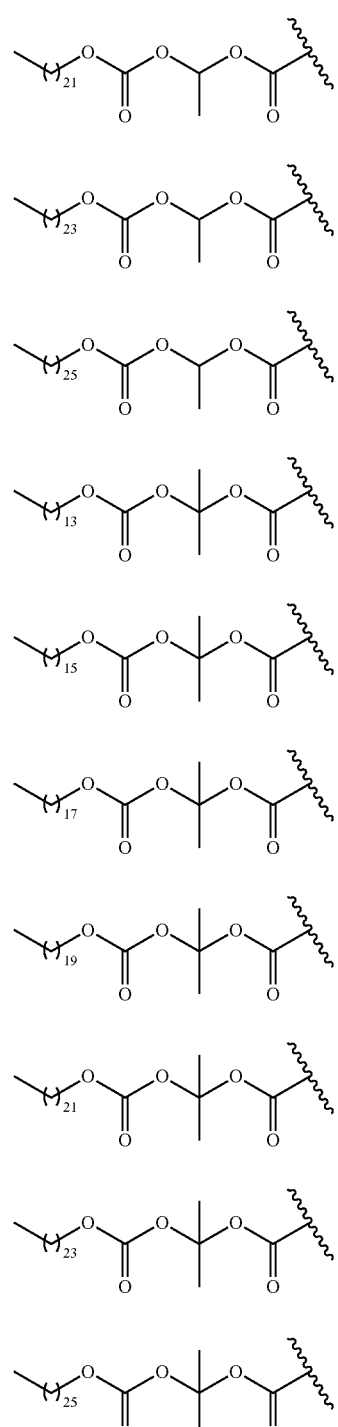
TABLE 2
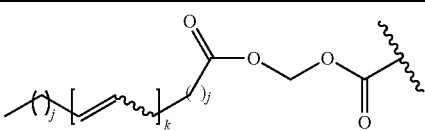

TABLE 2-continued
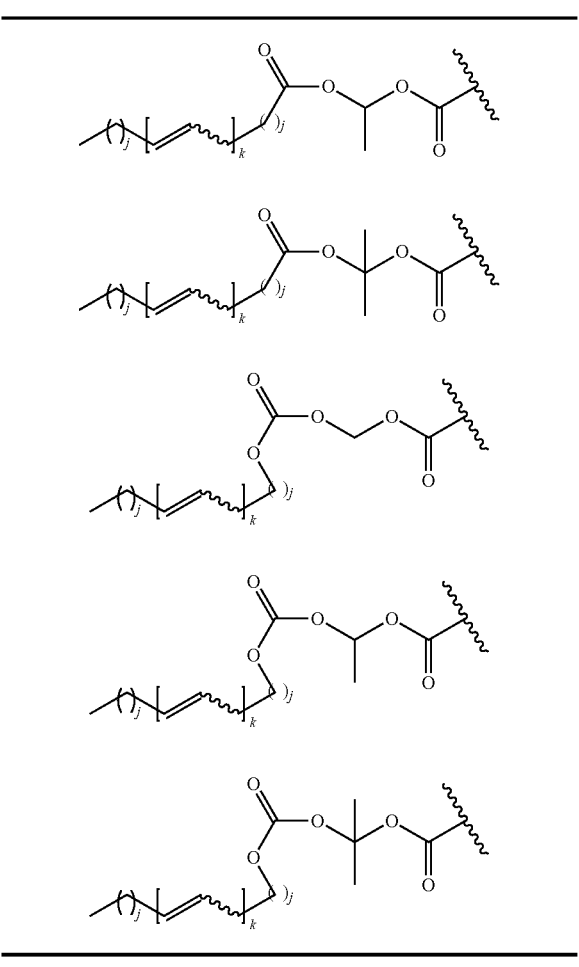
TABLE 3
TABLE 3-continued
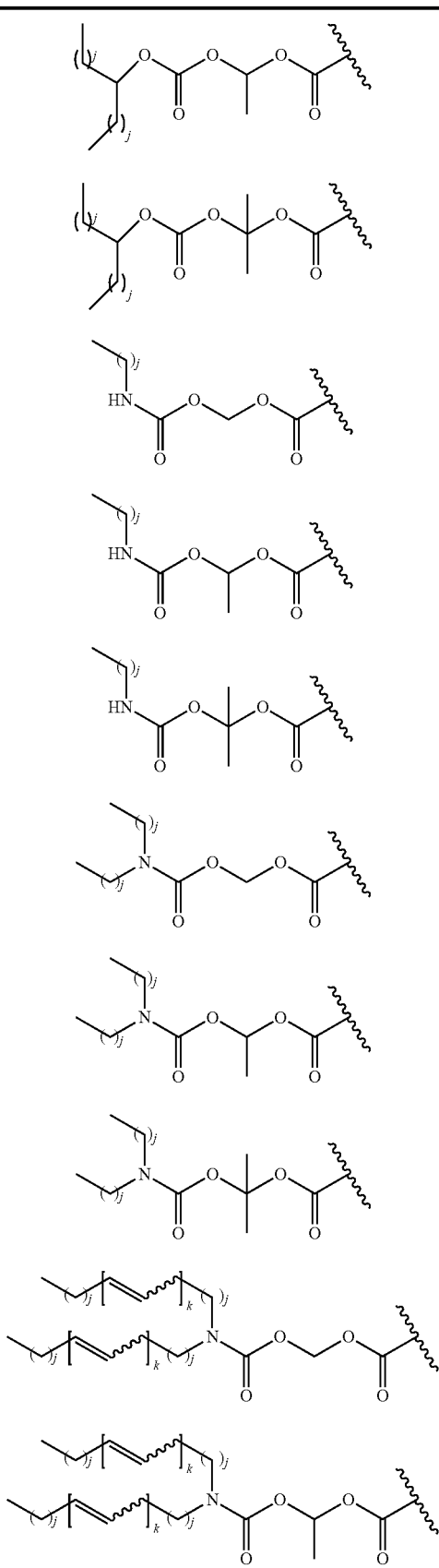

TABLE 3-continued

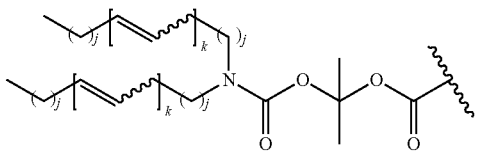

wherein each j is independently 0, 1, 2, 3, 4, 5, 6, 7, 8, 9, 10, 11, 12, 13, 14, 15, 16, 17, 18, 19, 20, 21, 22, 23, 24, 25, 26, or 27; and each k is independently 1, 2, 3, 4, 5, 6, 7, 8, 9, or 10.

In a further embodiment, the prodrug compounds of the invention are formulated with a biocompatible sustained release delivery system for delivery of the prodrug wherein the system is preferably capable of minimizing accelerated hydrolytic cleavage of the prodrug by minimizing exposure of the prodrug to water. Preferred delivery systems include biocompatible polymeric matrix delivery systems capable of minimizing the diffusion of water into the matrix having the prodrug dispersed therein.

In another embodiment, the invention provides a method of sustained delivery of a secondary amine-containing parent drug comprising administering to a subject an effective amount of a prodrug compound produced by substituting a labile, hydrophobic carbamate-linked prodrug moiety (represented by ——$R_1$) on the secondary amine nitrogen atom of the parent drug. Preferably the prodrug compound has decreased solubility under physiological conditions and sustained activity upon dosing compared to the parent drug compound.

Sustained release drug formulations often contain higher amounts of drugs than immediate release formulations. Functionality and safety of a sustained release formulation are based on a reliable and controlled rate of drug release from the formulation over an extended period of time after administration. The drug release profile of a formulation often depends on the chemical environment of the sustained release formulation, for example, on pH, ionic strength and presence of solvents such as ethanol.

The relatively high amount of drug that is present in a sustained release formulation can, in some instances, harm a patient if the formulation releases the drug at a rate that is faster than the intended controlled release rate. If the formulation releases the drug at a rate that is slower than the intended controlled release rate, the therapeutic efficacy of the drug can be reduced.

In most cases, partial or total failure of a sustained release formulation results in a rapid release of the drug into the bloodstream. This rapid release is generally faster than the intended sustained release of the drug from the formulation, and is sometimes referred to as Dose dumping can create severe consequences for a patient, including permanent harm and even death. Examples of drugs that can be fatal if the therapeutically beneficial dose is exceeded, e.g., by dose dumping, include pain medications such as opioids, as well as other agents active in the central nervous system. In those situations where dose dumping may not be fatal, dose dumping may at least be responsible for the side effect of sedation or coma in the patient.

In a preferred embodiment, a compound of the invention provides sustained delivery of the parent drug over hours, days, weeks or months when administered, for example, orally or parenterally, to a subject. For example, the compounds can provide sustained delivery of the parent drug for up to 7, 15, 30, 60, 75 or 90 days or longer. Without being bound by theory, it is believed that the compounds of the invention form an insoluble depot upon parenteral administration, for example subcutaneous, intramuscular or intraperitoneal injection.

The term "labile" as used herein refers to the capacity of the prodrug of the invention to undergo enzymatic and/or chemical cleavage in vivo thereby forming the parent drug. As used herein the term "prodrug" means a compounds as disclosed herein which is a labile derivative compound of a parent drug which when administered to a patient in vivo becomes cleaved by chemical and/or enzymatic hydrolysis thereby forming the parent drug such that a sufficient amount of the compound intended to be delivered to the patient is available for its intended therapeutic use in a sustained release manner.

The terms "sustained release", "sustained delivery" and "extended release" are used interchangeably herein to indicate that the prodrugs of the invention provide release of the parent drug by any mechanism including slow first-order kinetics of absorption or zero-order kinetics of absorption, such that the parent drug which is released from the prodrug provides a longer duration of action than the duration of action of the parent drug when administered alone (i.e. not as a prodrug of the invention). In accordance with the invention, "sustained release" of the prodrugs of the invention may include other pharmacokinetic indices such as a lower maximum concentration (Cmax) of parent drug in the blood and/or an extended period of time for the parent drug to reach maximum concentration in the blood (Tmax) as compared to the Cmax and Tmax when the parent drug is administered alone. Sustained release may also decrease concentration fluctuations in the body, as indicated by plasma concentration-time profiles.

It is understood that any of the parent prodrugs of the invention may be further substituted as that term is defined herein, so long as the substituted parent drug or parent prodrug, which when administered to a patient in vivo, becomes cleaved by chemical and/or enzymatic hydrolysis thereby releasing the parent drug moiety such that a sufficient amount of the compound intended to be delivered to the patient is available for its intended therapeutic use in a sustained release manner. A parent drug or parent prodrug may be further substituted for any purpose including, but not limited to, stabilization of the parent during synthesis of the prodrug and stabilization of the prodrug for administration to the patient.

In one embodiment, the present invention provides a method of treating a neurological or psychiatric disorder or disease in a patient in need thereof, by conjugating a labile moiety to a parent drug useful for treating a neurological or psychiatric disorder or disease. The method comprises administering to the subject a therapeutically effective amount of a compound of the invention or a pharmaceutically acceptable salt thereof.

The term "neurological or psychiatric disorder", as this term is used herein, is a disease or disorder of the central nervous system that is manifested in mood and/or behavioral abnormalities. Examples of neurological or psychiatric disorders include, but are not limited to, disorders such as cerebral deficit subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, Parkinsonism, muscular spasms and disorders associated with muscular spasticity including tremors, epilepsy, convulsions, cerebral deficits secondary to prolonged status epilepticus, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, social phobia, obsessive compulsive disorder, and post-traumatic stress disorder (PTSD)), attention deficit disorder (ADD), attention deficit hyperactivity disorder (ADHD), mood disorders (including depression, mania, bipolar disorders), circadian rhythm disorders (including jet lag and shift work), trigeminal neuralgia, hearing loss, tinnitus, macular degeneration of the eye, emesis, brain edema, pain (including acute and chronic pain states, severe pain, intractable pain, neuropathic pain, inflammatory pain, and post-traumatic pain), tardive dyskinesia, sleep disorders (including narcolepsy), attention deficit/hyperactivity disorder, and conduct disorder.

In another embodiment, the present invention provides a method of treating cardiac and cardiovascular disorders such as angina, arrhythmia, and hypertension, in a patient in need thereof. The method comprises administering to the subject a therapeutically effective amount of a compound of the invention or a pharmaceutically acceptable salt thereof.

The invention further relates to the treatment of fever, diabetes, allergy, asthma, infection, inflammation, and ulcers in a patient in need thereof, comprising administering to the subject a therapeutically effective amount of a compound of the invention or a pharmaceutically acceptable salt thereof.

The invention further relates to the treatment of sleep modulation comprising administration of a compound of Formula I. Sleep modulation includes decreasing the time to sleep onset, increasing the average sleep bout length, and increasing the maximum sleep bout length.

The term "treatment" refers to any process, action, application, therapy, or the like, wherein a mammal, including a human being, is subject to medical aid with the object of improving the mammal's condition, directly or indirectly.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha- (α), beta- (β) and gamma- (γ) cyclodextrins; starches such as corn starch and potato starch; cellulose and its derivatives such as sodium carboxymethylcellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and anti-oxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is parenteral administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, acetamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. INTRALIPID® is an intravenous fat emulsion containing 10-30% soybean oil, 1-10% egg yolk phospholipids, 1-10% glycerin and water. LIPOSYN® is also an intravenous fat emlusion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Additional sustained release in accordance with the invention may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

In one preferred embodiment, the formulation provides a sustained release delivery system that is capable of minimizing the exposure of the prodrug to water. This can be accomplished by formulating the prodrug with a sustained release delivery system that is a polymeric matrix capable of minimizing the diffusion of water into the matrix. Suitable polymers comprising the matrix include poly(lactide) (PLA) polymers and the lactide/(glycolide) (PLGA) copolymers as described earlier.

Alternatively, the sustained release delivery system may comprise poly-anionic molecules or resins that are suitable for injection or oral delivery. Suitable polyanionic molecules include cyclodextrins and polysulfonates formulated to form a poorly soluble mass that minimizes exposure of the prodrug to water and from which the prodrug slowly leaves. Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

In preferred embodiments, the compounds of the invention, or pharmaceutical compositions comprising one or more compounds of the invention, are administered parenterally, for example, by intramuscular, subcutaneous or intraperitoneal injection. Without being bound by theory, it is believed that upon injection, compounds of the invention form an insoluble or sparingly soluble depot from which prodrug molecules are released over time.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, the possibility of co-usage with other agents and the duration of release of the parent drug. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The compounds of this invention can be administered to a human or other animal in single or in divided doses, and can be in amounts for example between 0.1 to about 2,000 mg. Single dose compositions may contain such amounts or submultiples thereof to make up the daily, weekly, biweekly, triweekly or monthly dose. In general, treatment regimens according to the present invention comprise administration to a patient in need of such treatment from about 5 mg to about 1000 mg of the compound(s) of this invention on a daily, weekly, biweekly, triweekly or monthly singly dose.

The compounds of the invention can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation.

In a preferred embodiment, the administration of the compounds of the invention results in sustained or controlled release. The compounds of the invention can be administered with a dosage ranging from about 0.1 to about 2000 mg, Alternatively dosages can be between about 1 mg and about 1000 mg/dose, or between about 5 and about 800 every day, every week, every two weeks, every three weeks or every month, or according to the requirements of the particular drug. Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Preferred compounds of the invention exhibit sustained activity following dosing compared to dosing with the parent drug. For example, when administered by the same route in the same amount (as measured by equivalents of parent drug), the compounds of the invention provide sustained therapeutic serum levels of parent drug for a significantly longer time than the parent drug. Such administration can be oral, with sustained delivery over hours, or parenteral, with sustained delivery over days, weeks or months.

Representative compounds of the invention include the compounds set forth in Table 4 below.

TABLE 4

| Compound# | Structure |
| --- | --- |
| 1. | 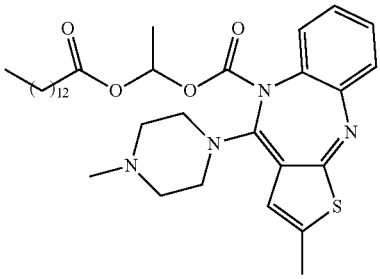 |
| 2. | 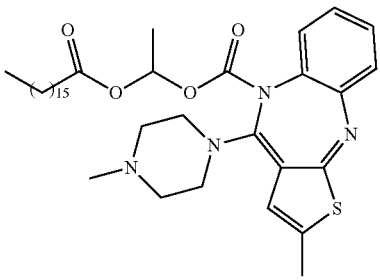 |

TABLE 4-continued

| Compound# | Structure |
|---|---|
| 3. | [structure: olanzapine N-carbamate with -O-CH(CH3)-O-C(=O)-(CH2)17-CH3 chain] |
| 4. | [structure: olanzapine N-carbamate with -O-CH(CH3)-O-C(=O)-(CH2)19-CH3 chain] |
| 5. | [structure: olanzapine N-carbamate with -O-CH(CH3)-O-C(=O)-(CH2)21-CH3 chain] |
| 6. | [structure: olanzapine N-C(=O)-O-CH2-O-C(=O)-long alkyl chain] |
| 7. | [structure: olanzapine N-C(=O)-O-CH2-O-C(=O)-long alkyl chain] |

TABLE 4-continued

| Compound# | Structure |
|---|---|
| 8. | 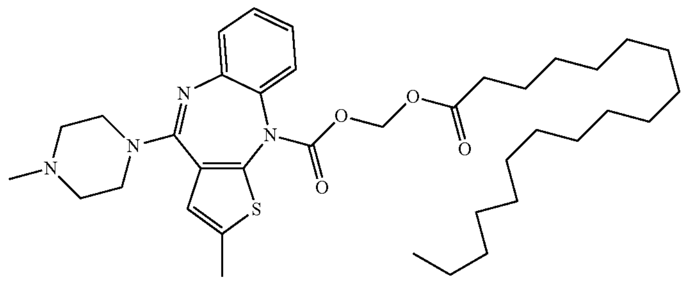 [SMILES: CCCCCCCCCCCCCCCCCC(=O)OCOC(=O)N1c2ccccc2N=C(N2CCN(C)CC2)c2cc(C)sc21] |
| 9. | 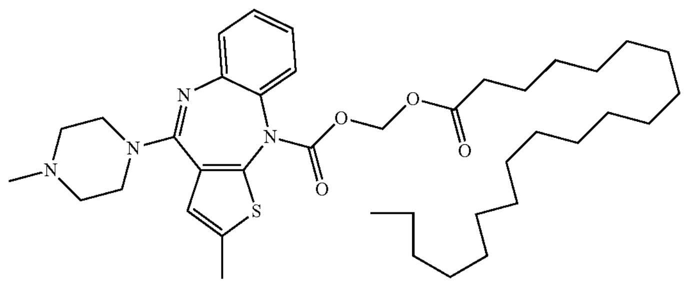 [SMILES: CCCCCCCCCCCCCCCCCCCC(=O)OCOC(=O)N1c2ccccc2N=C(N2CCN(C)CC2)c2cc(C)sc21] |
| 10. | 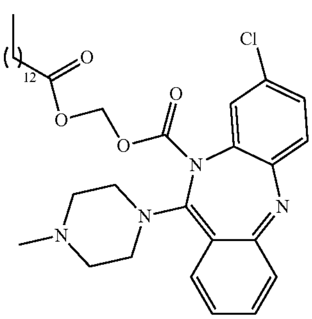 |
| 11. | 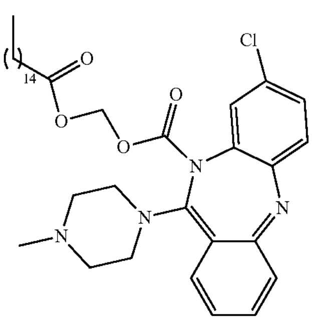 |
| 12. | 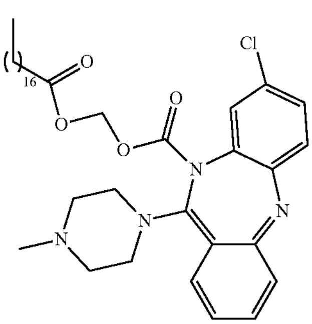 |

TABLE 4-continued

| Compound# | Structure |
|---|---|
| 13. | 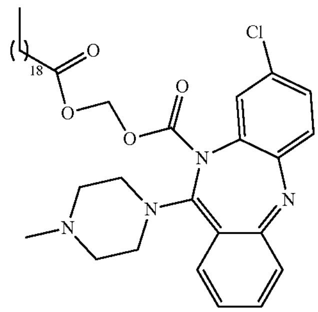 |
| 14. | 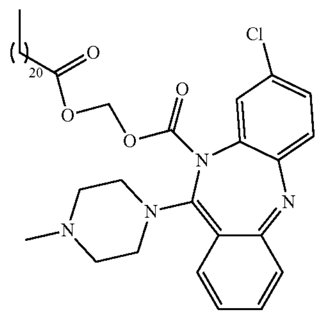 |
| 15. | 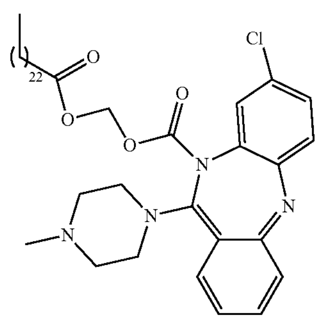 |
| 16. | 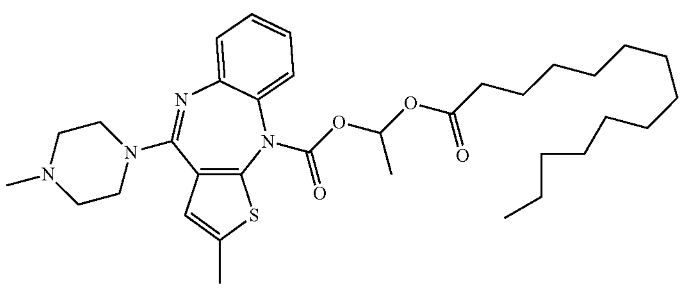 [SMILES: CCCCCCCCCCCCCC(=O)OC(C)OC(=O)N1c2ccccc2N=C(N2CCN(C)CC2)c2cc(C)sc21] |
| 17. | 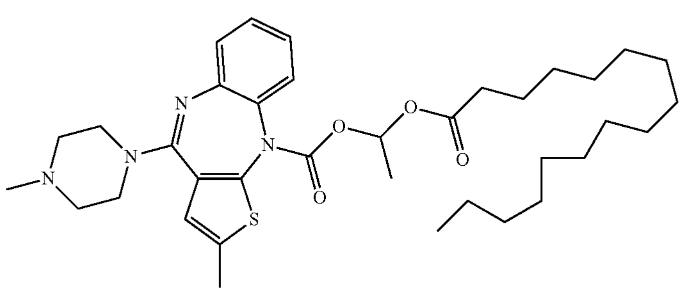 [SMILES: CCCCCCCCCCCCCCCC(=O)OC(C)OC(=O)N1c2ccccc2N=C(N2CCN(C)CC2)c2cc(C)sc21] |

TABLE 4-continued
| Compound# | Structure |
|---|---|
| 18. | 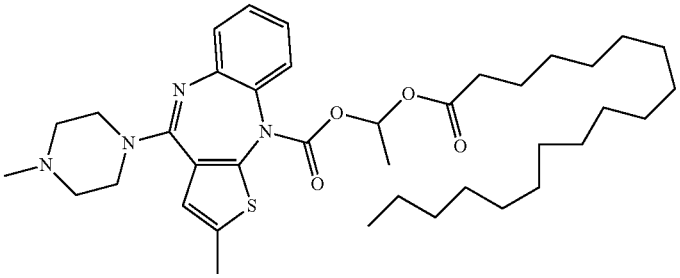 [SMILES: CCCCCCCCCCCCCCCCCC(=O)OC(C)OC(=O)N1c2ccccc2N=C(N2CCN(C)CC2)c2cc(C)sc21] |
| 19. | 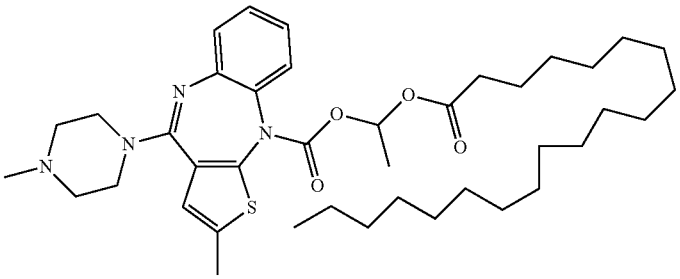 [SMILES: CCCCCCCCCCCCCCCCCCCC(=O)OC(C)OC(=O)N1c2ccccc2N=C(N2CCN(C)CC2)c2cc(C)sc21] |
| 20. | 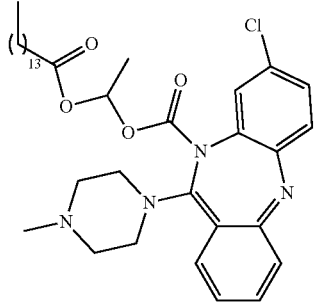 |
| 21. | 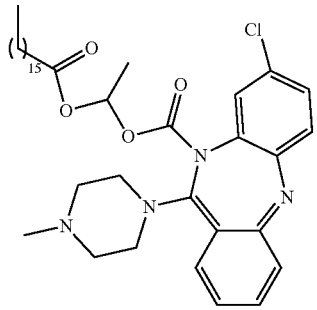 |
| 22. | 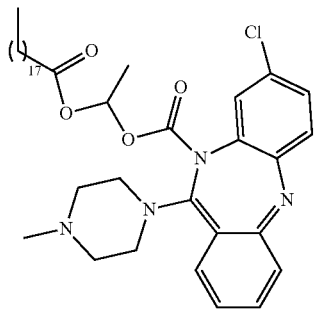 |

TABLE 4-continued

| Compound# | Structure |
|---|---|
| 23. | (chemical structure: chlorinated dibenzodiazepine with N-methylpiperazine, carbamate linker, ethylidene ester of fatty acid with (CH₂)₁₉ chain) |
| 24. | (chemical structure: chlorinated dibenzodiazepine with N-methylpiperazine, carbamate linker, ethylidene ester of fatty acid with (CH₂)₂₁ chain) |
| 25. | (chemical structure: duloxetine-like scaffold with naphthyloxy and thiophene groups, N-methyl carbamate linked via ethylidene ester to fatty acid with (CH₂)₁₂ chain) |
| 26. | (chemical structure: duloxetine-like scaffold with naphthyloxy and thiophene groups, N-methyl carbamate linked via ethylidene ester to fatty acid with (CH₂)₁₆ chain) |

TABLE 4-continued
| Compound# | Structure |
|---|---|
| 27. | 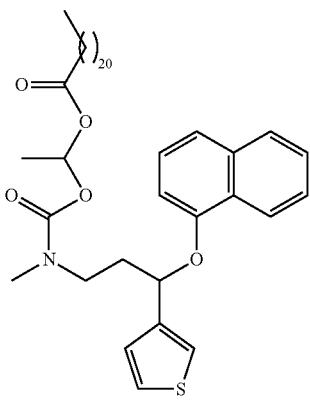 |
| 28. | 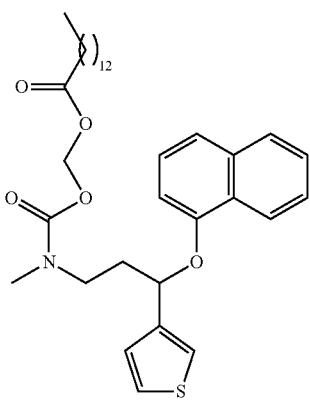 |
| 29. | 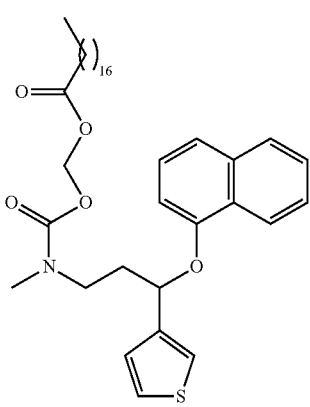 |
| 30. | 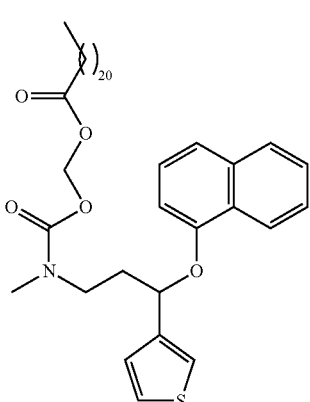 |

TABLE 4-continued
| Compound# | Structure |
|---|---|
| 31. | 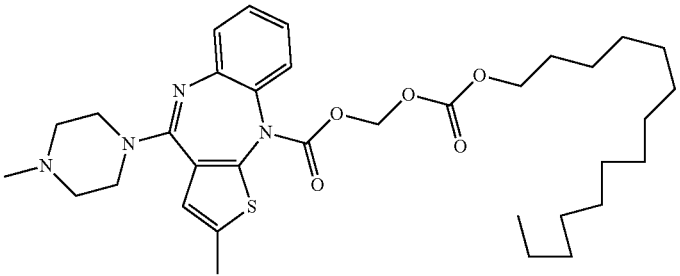 [SMILES: CCCCCCCCCCCCCCOC(=O)OCOC(=O)N1c2ccccc2N=C(N2CCN(C)CC2)c2cc(C)sc21] |
| 32. | 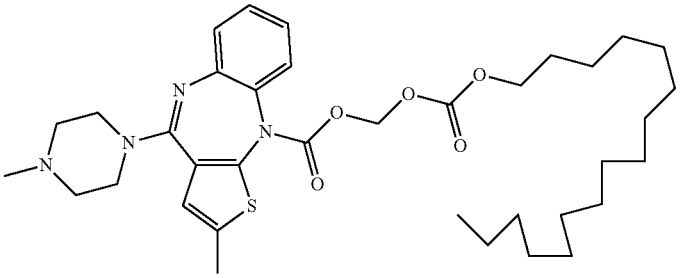 [SMILES: CCCCCCCCCCCCCCCCOC(=O)OCOC(=O)N1c2ccccc2N=C(N2CCN(C)CC2)c2cc(C)sc21] |
| 33. | 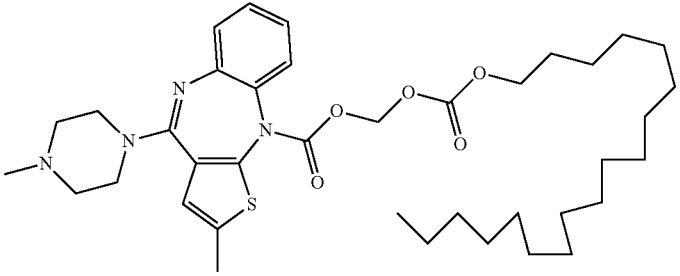 [SMILES: CCCCCCCCCCCCCCCCCCOC(=O)OCOC(=O)N1c2ccccc2N=C(N2CCN(C)CC2)c2cc(C)sc21] |
| 34. | 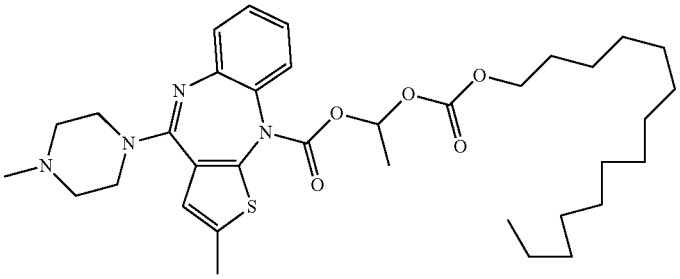 [SMILES: CCCCCCCCCCCCCCOC(=O)OC(C)OC(=O)N1c2ccccc2N=C(N2CCN(C)CC2)c2cc(C)sc21] |
| 35. | 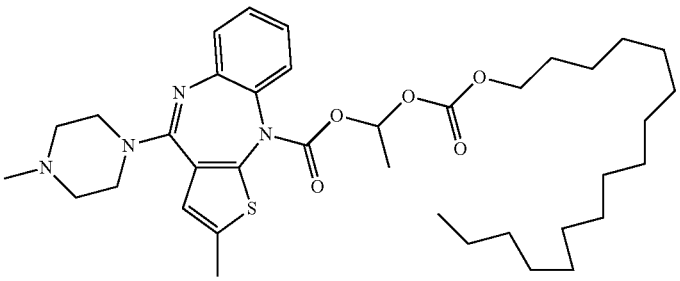 [SMILES: CCCCCCCCCCCCCCCCOC(=O)OC(C)OC(=O)N1c2ccccc2N=C(N2CCN(C)CC2)c2cc(C)sc21] |

TABLE 4-continued
| Compound# | Structure |
|---|---|
| 36. | 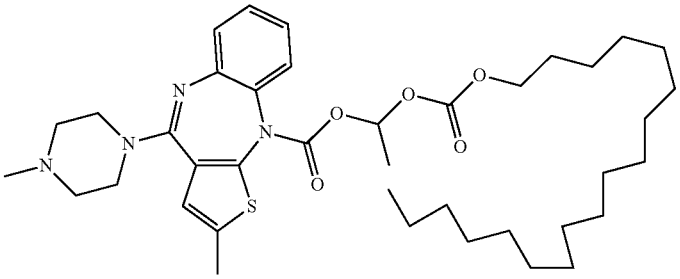 [SMILES: CCCCCCCCCCCCCCCCCCOC(=O)OC(C)OC(=O)N1c2ccccc2N=C(N2CCN(C)CC2)c2cc(C)sc21] |
| 37. | 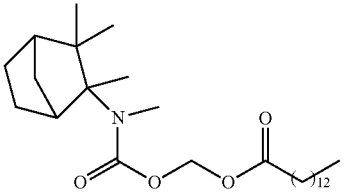 |
| 38. | 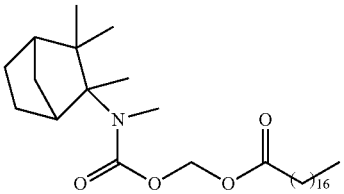 |
| 39. | 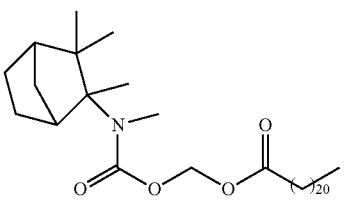 |
| 40. | 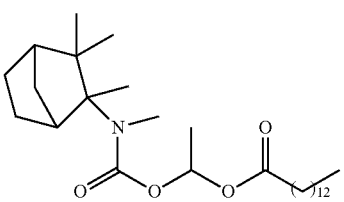 |
| 41. | 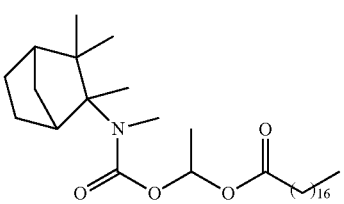 |
| 42. | 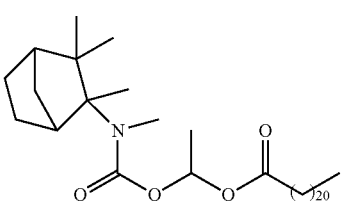 |

TABLE 4-continued

| Compound# | Structure |
|---|---|
| 43. | *(chemical structure: 2-amino-4,5,6,7-tetrahydrobenzothiazole with N-propyl carbamate, —OCH₂—O—C(O)—(CH₂)₁₂—CH₃)* |
| 44. | *(chemical structure: same core, —OCH₂—O—C(O)—(CH₂)₁₆—CH₃)* |
| 45. | *(chemical structure: same core, —OCH₂—O—C(O)—(CH₂)₂₀—CH₃)* |
| 46. | *(chemical structure: same core, —OCH(CH₃)—O—C(O)—(CH₂)₁₂—CH₃)* |
| 47. | *(chemical structure: same core, —OCH(CH₃)—O—C(O)—(CH₂)₁₆—CH₃)* |

TABLE 4-continued

| Compound# | Structure |
|---|---|
| 48. | *(structure: 2-amino-4,5,6,7-tetrahydrobenzothiazole with N-propyl carbamate, O-CH(CH₃)-O-C(=O)-(CH₂)₂₀-)* |
| 49. | *(structure: N-propargyl-N-(indan-1-yl) carbamate, -O-CH₂-O-C(=O)-(CH₂)₁₂-)* |
| 50. | *(structure: N-propargyl-N-(indan-1-yl) carbamate, -O-CH₂-O-C(=O)-(CH₂)₁₆-)* |
| 51. | *(structure: N-propargyl-N-(indan-1-yl) carbamate, -O-CH₂-O-C(=O)-(CH₂)₂₀-)* |
| 52. | *(structure: N-propargyl-N-(indan-1-yl) carbamate, -O-CH(CH₃)-O-C(=O)-(CH₂)₁₂-)* |
| 53. | *(structure: N-propargyl-N-(indan-1-yl) carbamate, -O-CH(CH₃)-O-C(=O)-(CH₂)₁₆-)* |
| 54. | *(structure: N-propargyl-N-(indan-1-yl) carbamate, -O-CH(CH₃)-O-C(=O)-(CH₂)₂₀-)* |

TABLE 4-continued

| Compound# | Structure |
|---|---|
| 55. | 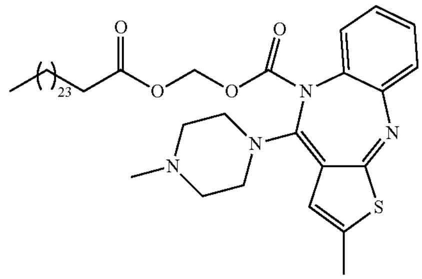 |
| 56. | 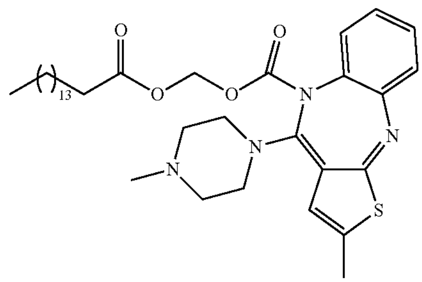 |
| 57. | 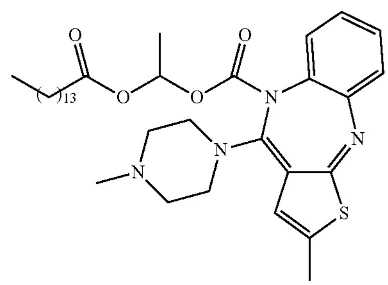 |
| 58. | 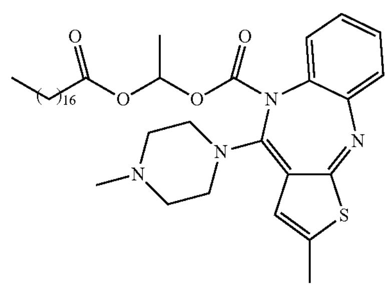 |
| 59. | 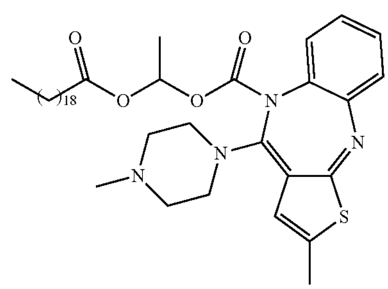 |

TABLE 4-continued
| Compound# | Structure |
|---|---|
| 60. | 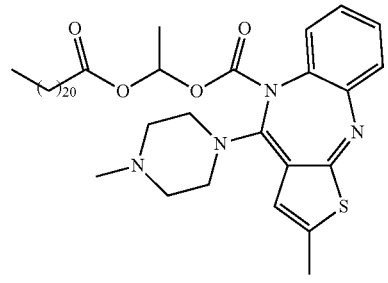 |
| 61. | 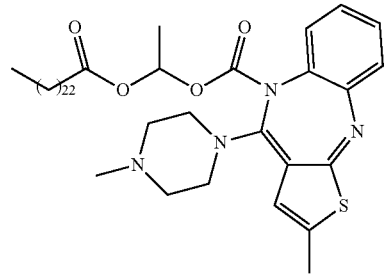 |
| 62. | 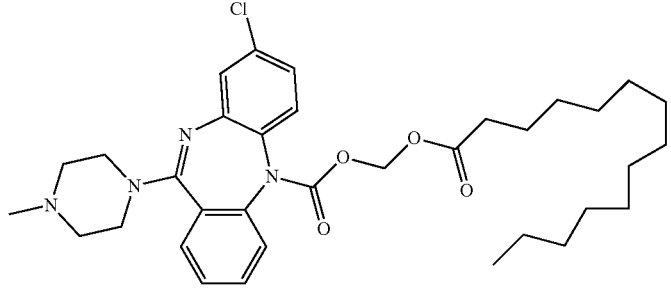 [SMILES: CCCCCCCCCCCCCC(=O)OCOC(=O)N1c2ccc(Cl)cc2N=C(N2CCN(C)CC2)c2ccccc21] |
| 63. | 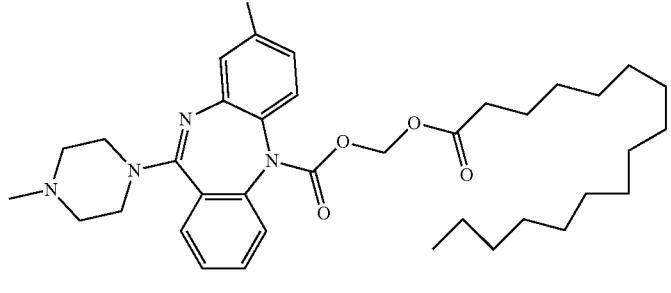 |
| 64. | 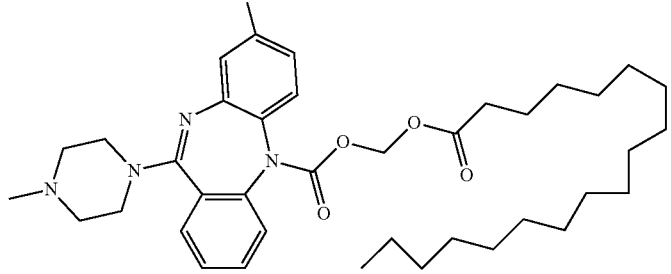 |

TABLE 4-continued
| Compound# | Structure |
|---|---|
| 65. | 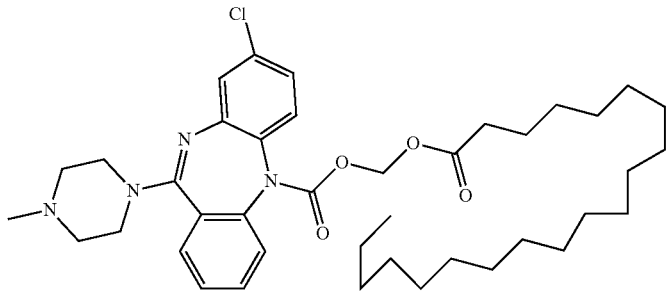 [SMILES: CCCCCCCCCCCCCCCCCCCC(=O)OCOC(=O)N1c2ccc(Cl)cc2N=C(N2CCN(C)CC2)c2ccccc21] |
| 66. | 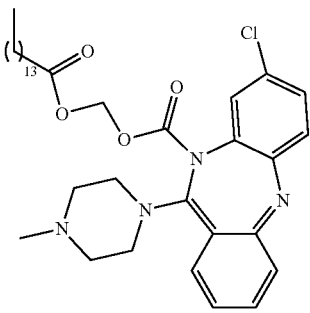 |
| 67. | 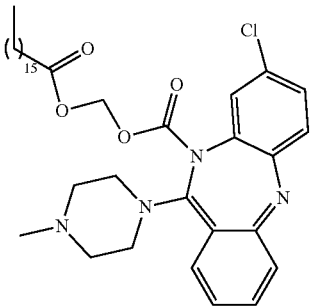 |
| 68. | 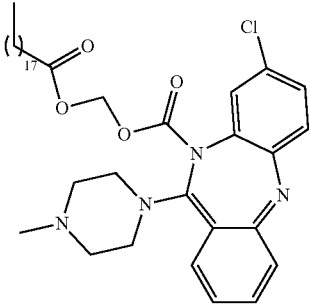 |
| 69. | 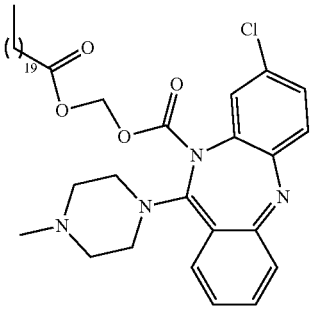 |

TABLE 4-continued

| Compound# | Structure |
| --- | --- |
| 70. | 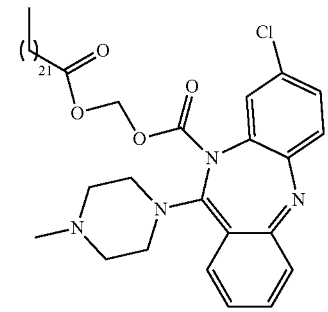 |
| 71. | 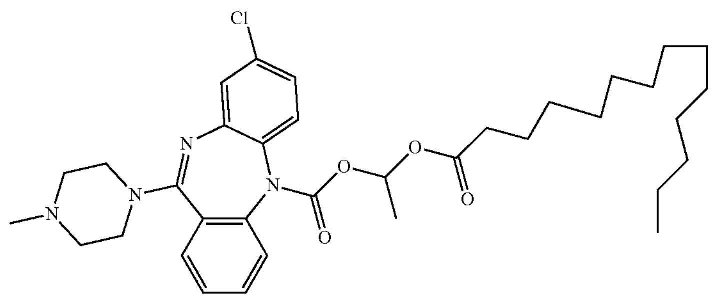 [SMILES: CCCCCCCCCCCCCC(=O)OC(C)OC(=O)N1c2ccc(Cl)cc2N=C(N2CCN(C)CC2)c2ccccc21] |
| 72. | 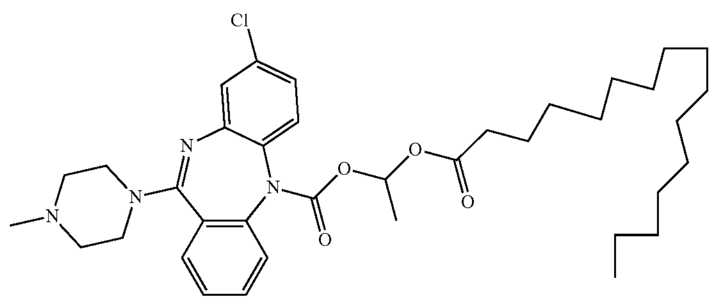 [SMILES: CCCCCCCCCCCCCCCC(=O)OC(C)OC(=O)N1c2ccc(Cl)cc2N=C(N2CCN(C)CC2)c2ccccc21] |
| 73. | 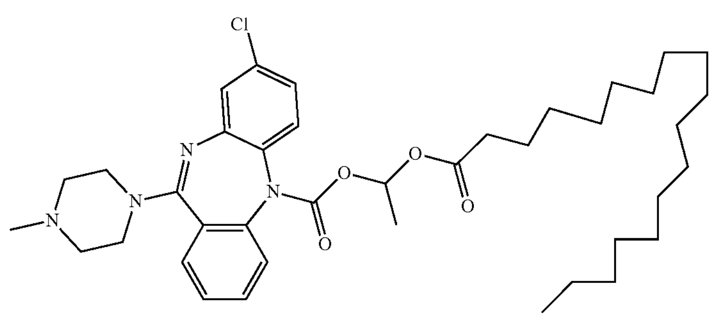 [SMILES: CCCCCCCCCCCCCCCCCC(=O)OC(C)OC(=O)N1c2ccc(Cl)cc2N=C(N2CCN(C)CC2)c2ccccc21] |
| 74. | 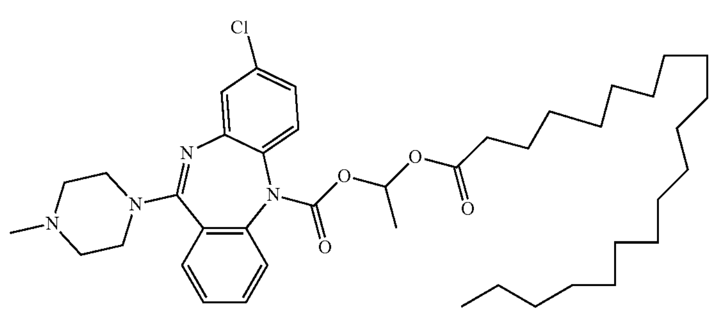 [SMILES: CCCCCCCCCCCCCCCCCCCC(=O)OC(C)OC(=O)N1c2ccc(Cl)cc2N=C(N2CCN(C)CC2)c2ccccc21] |

TABLE 4-continued

| Compound# | Structure |
|---|---|
| 75. | 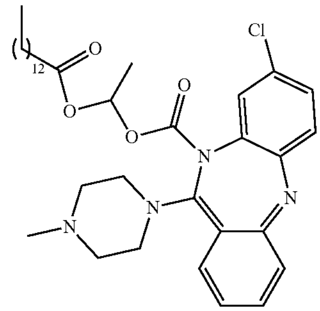 |
| 76. | 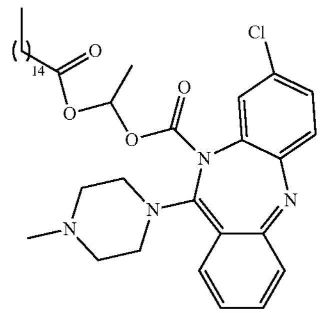 |
| 77. | 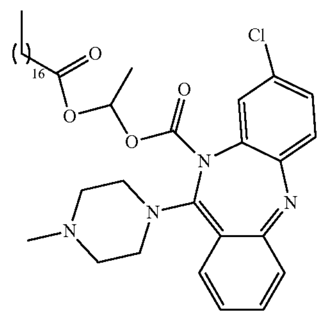 |
| 78. | 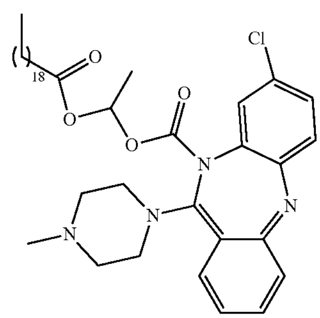 |
| 79. | 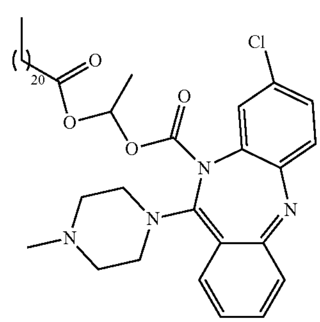 |

TABLE 4-continued

| Compound# | Structure |
|---|---|
| 80. | 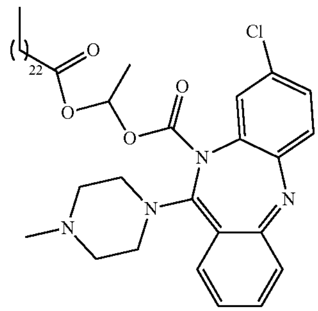 |
| 81. | 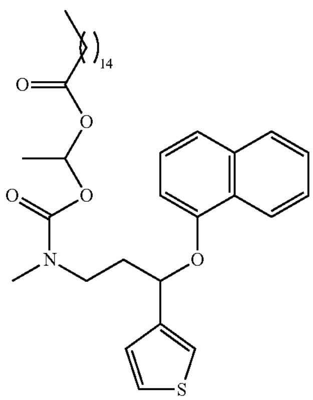 |
| 82. | 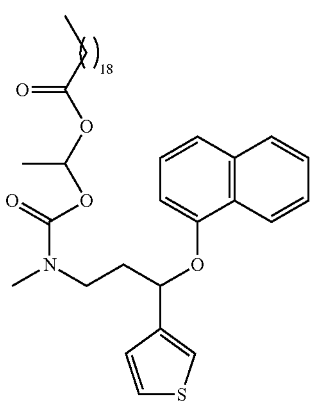 |
| 83. | 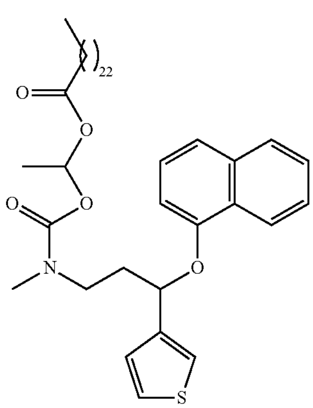 |

TABLE 4-continued

| Compound# | Structure |
|---|---|
| 84. | 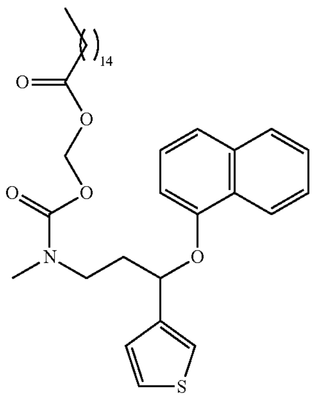 |
| 85. | 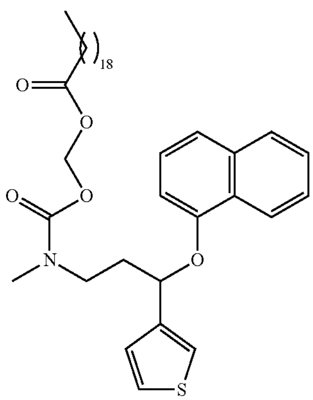 |
| 86. | 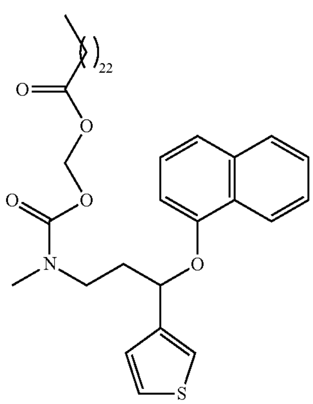 |
| 87. | 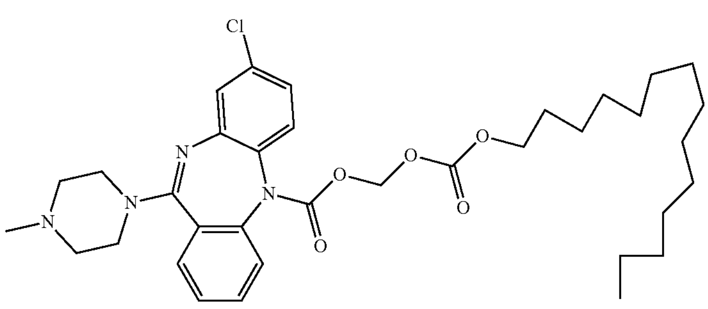 [SMILES: CCCCCCCCCCCCCCOC(=O)OCOC(=O)N1c2ccc(Cl)cc2N=C(N2CCN(C)CC2)c2ccccc21] |

TABLE 4-continued
| Compound# | Structure |
|---|---|
| 88. | 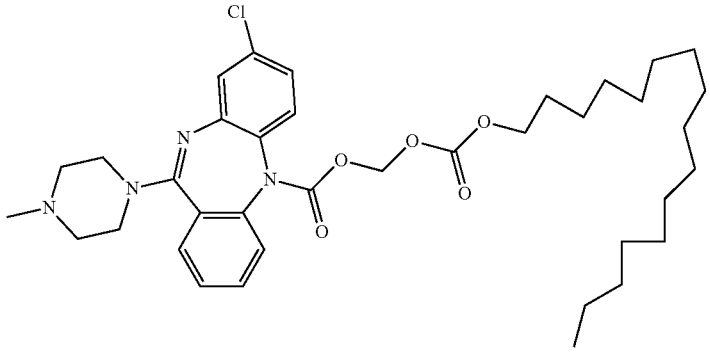 [SMILES: CCCCCCCCCCCCCCCCOC(=O)OCOC(=O)N1c2ccc(Cl)cc2N=C(N2CCN(C)CC2)c2ccccc21] |
| 89. | 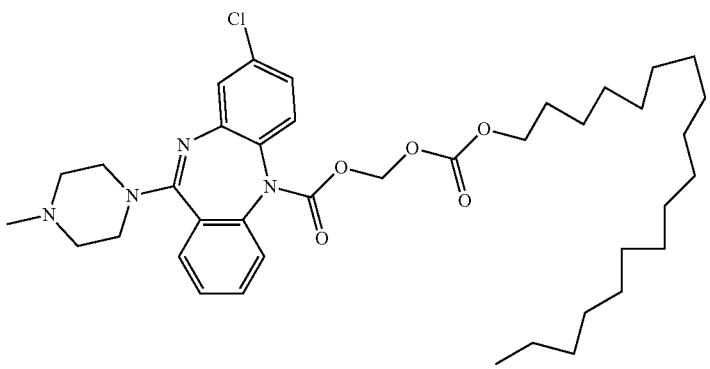 |
| 90. | 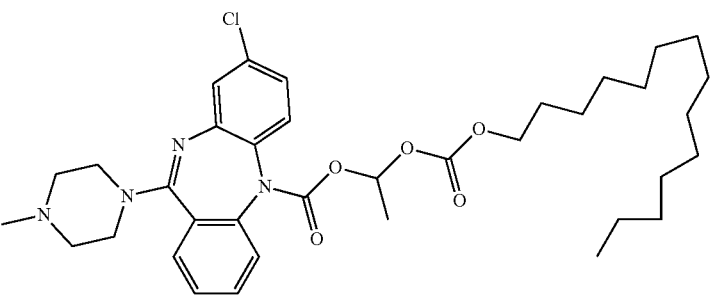 [SMILES: CCCCCCCCCCCCCCOC(=O)OC(C)OC(=O)N1c2ccc(Cl)cc2N=C(N2CCN(C)CC2)c2ccccc21] |
| 91. | 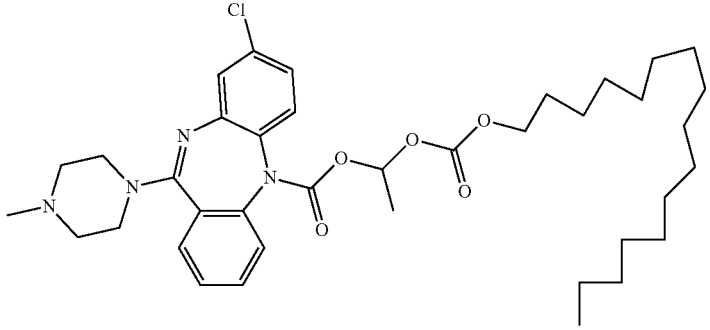 [SMILES: CCCCCCCCCCCCCCCCOC(=O)OC(C)OC(=O)N1c2ccc(Cl)cc2N=C(N2CCN(C)CC2)c2ccccc21] |

TABLE 4-continued

| Compound# | Structure |
|---|---|
| 92. | (structure image) |
| 93. | (structure image) |
| 94. | (structure image) |
| 95. | (structure image) |
| 96. | (structure image) |
| 97. | (structure image) |
| 98. | (structure image) |

TABLE 4-continued

| Compound# | Structure |
|---|---|
| 99. | (structure: 2-amino-4,5,6,7-tetrahydrobenzothiazole with N-propyl carbamate, -O-CH2-O-C(=O)-(CH2)14-CH3) |
| 100. | (structure: 2-amino-4,5,6,7-tetrahydrobenzothiazole with N-propyl carbamate, -O-CH2-O-C(=O)-(CH2)18-CH3) |
| 101. | (structure: 2-amino-4,5,6,7-tetrahydrobenzothiazole with N-propyl carbamate, -O-CH2-O-C(=O)-(CH2)22-CH3) |
| 102. | (structure: 2-amino-4,5,6,7-tetrahydrobenzothiazole with N-propyl carbamate, -O-CH(CH3)-O-C(=O)-(CH2)14-CH3) |
| 103. | (structure: 2-amino-4,5,6,7-tetrahydrobenzothiazole with N-propyl carbamate, -O-CH(CH3)-O-C(=O)-(CH2)18-CH3) |

US 11,225,490 B2
TABLE 4-continued
| Compound# | Structure |
|---|---|
| 104. | 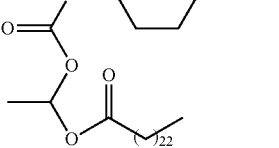 |
| 105. | 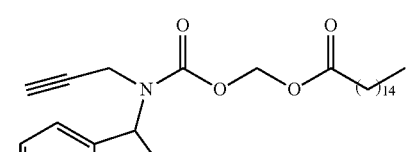 |
| 106. | 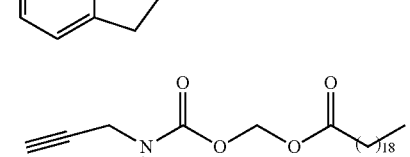 |
| 107. | 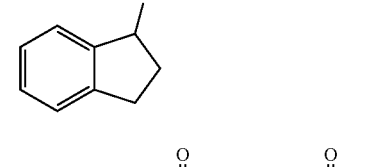 |
| 108. | 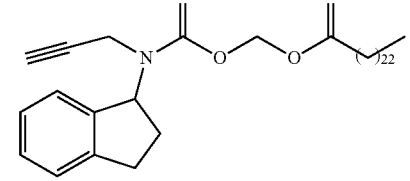 |
| 109. | 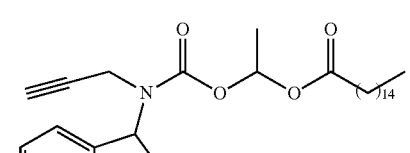 |
| 110. | 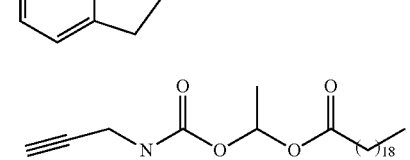 |

TABLE 4-continued

| Compound# | Structure |
|---|---|
| 111. | 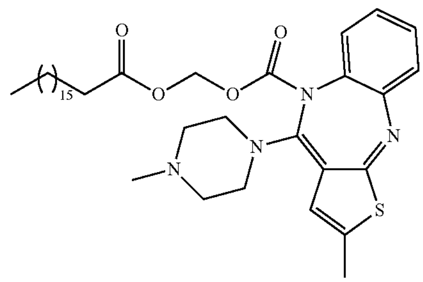 |
| 112. | 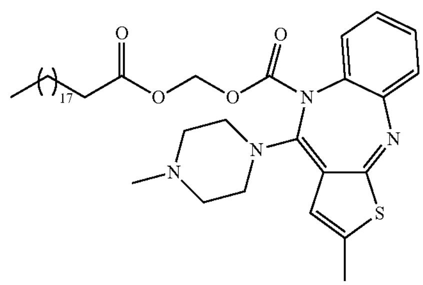 |
| 113. | 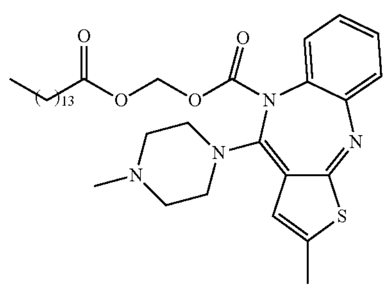 |
| 114. | 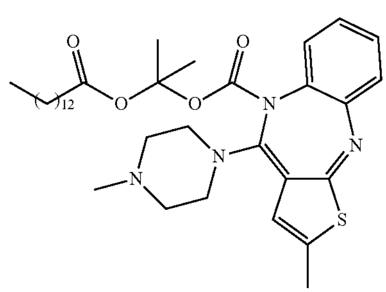 |
| 115. | 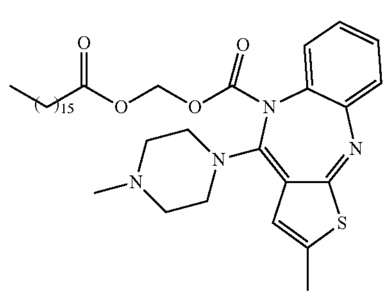 |

TABLE 4-continued

| Compound# | Structure |
|---|---|
| 116. | 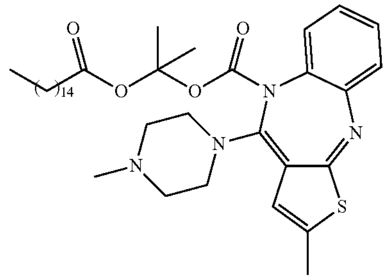 |
| 117. | 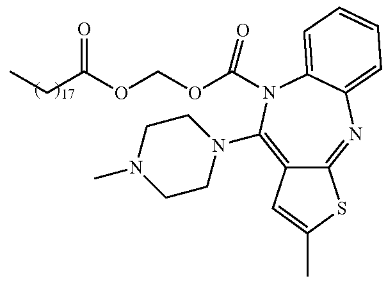 |
| 118. | 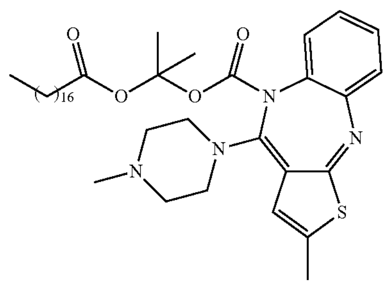 |
| 119. | 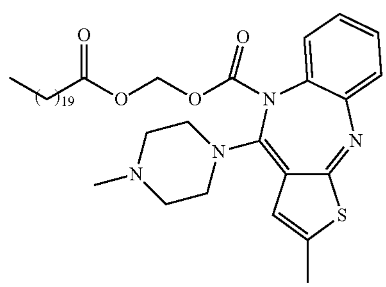 |
| 120. | 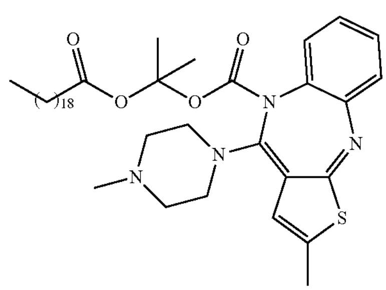 |

TABLE 4-continued

| Compound# | Structure |
|---|---|
| 121. | 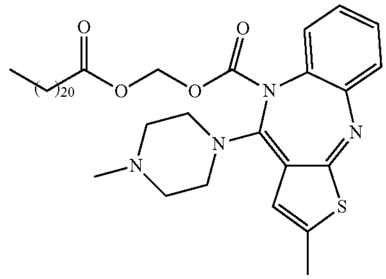 |
| 122. | 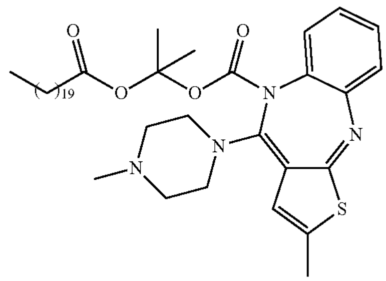 |
| 123. | 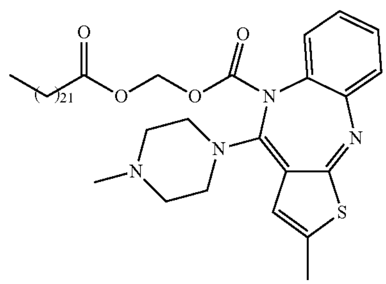 |
| 124. | 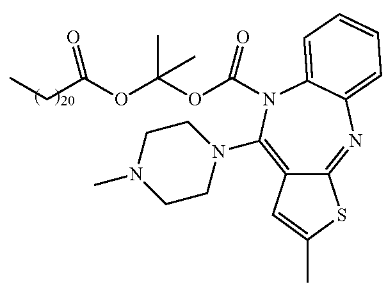 |
| 125. | 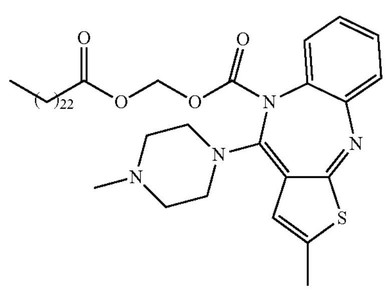 |

TABLE 4-continued

| Compound# | Structure |
|---|---|
| 126. | 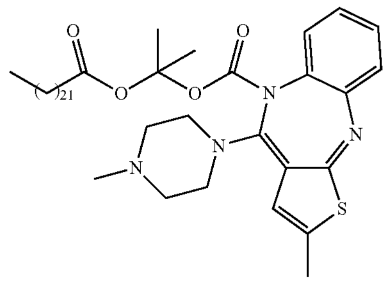 |
| 127. | 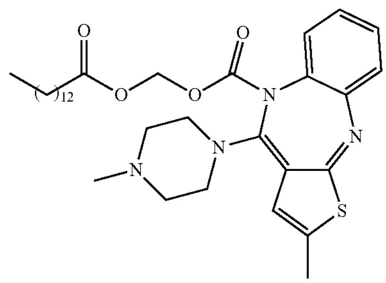 |
| 128. | 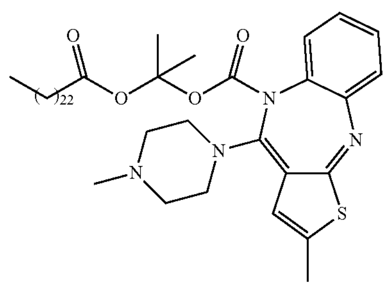 |
| 129. | 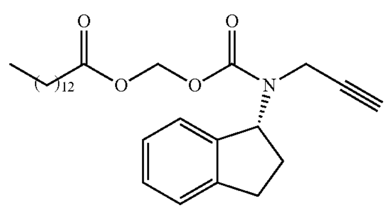 |
| 130. | 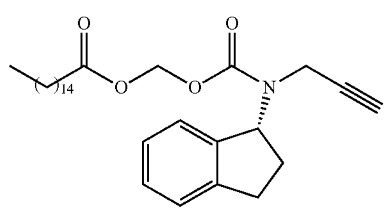 |
| 131. | 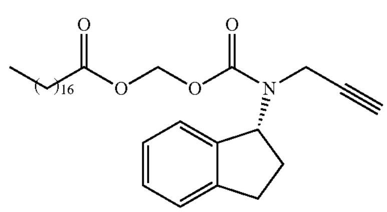 |

TABLE 4-continued
| Compound# | Structure |
|---|---|
| 132. | 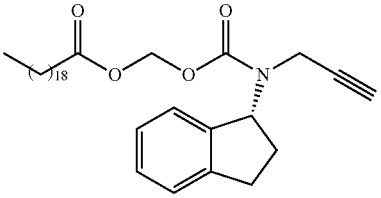 |
| 133. | 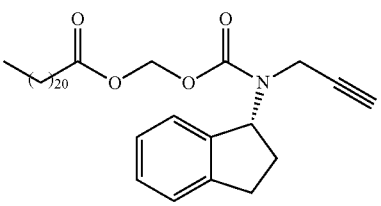 |
| 134. | 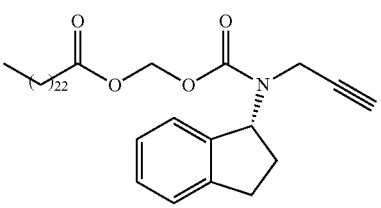 |
| 135. | 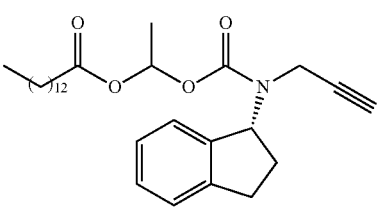 |
| 136. | 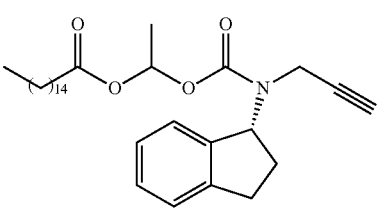 |
| 137. | 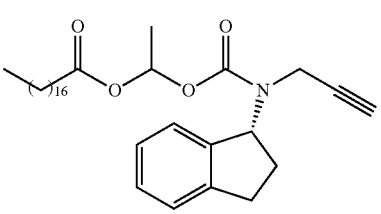 |
| 138. | 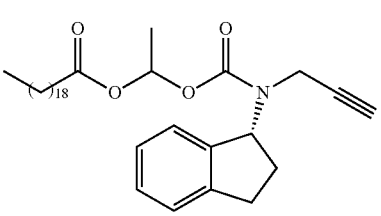 |

TABLE 4-continued

| Compound# | Structure |
|---|---|
| 139. | 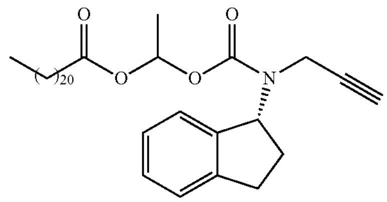 |
| 140. | 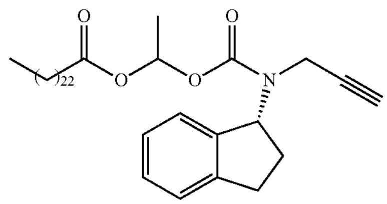 |
| 141. | 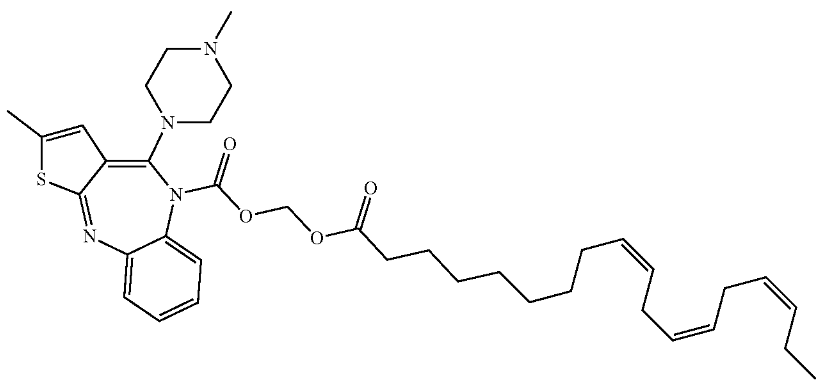 [SMILES: CC/C=C\C/C=C\C/C=C\CCCCCCCC(=O)OCOC(=O)N1C(N2CCN(C)CC2)=c2cc(C)sc2=Nc2ccccc21] |
| 142. | 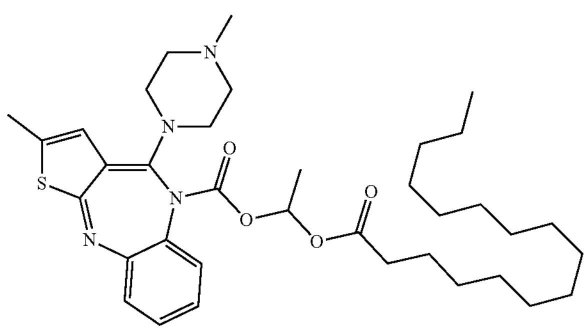 [SMILES: CCCCCCCCCCCCCCCC(=O)OC(C)OC(=O)N1C(N2CCN(C)CC2)=c2cc(C)sc2=Nc2ccccc21] |
| 143. | 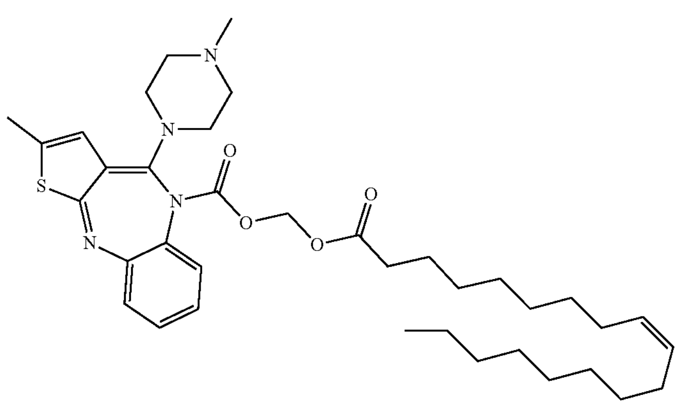 [SMILES: CCCCCCCC/C=C\CCCCCCCC(=O)OCOC(=O)N1C(N2CCN(C)CC2)=c2cc(C)sc2=Nc2ccccc21] |

TABLE 4-continued

| Compound# | Structure |
|---|---|
| 144. | 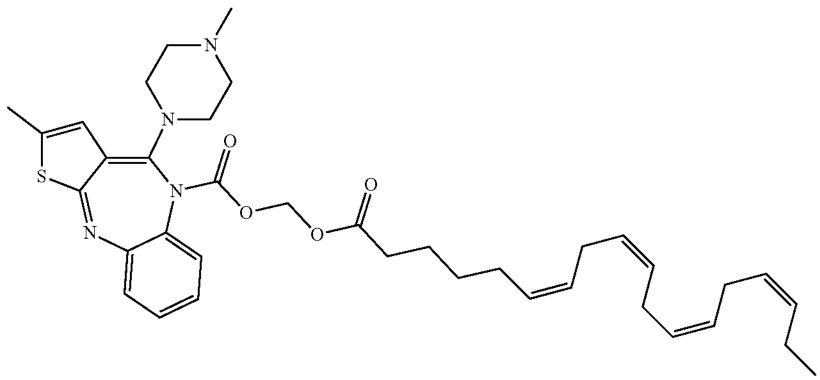 [SMILES: CC/C=C\C/C=C\C/C=C\C/C=C\CCCCC(=O)OCOC(=O)N1C(N2CCN(C)CC2)=c2cc(C)sc2=Nc2ccccc21] |
| 145. | 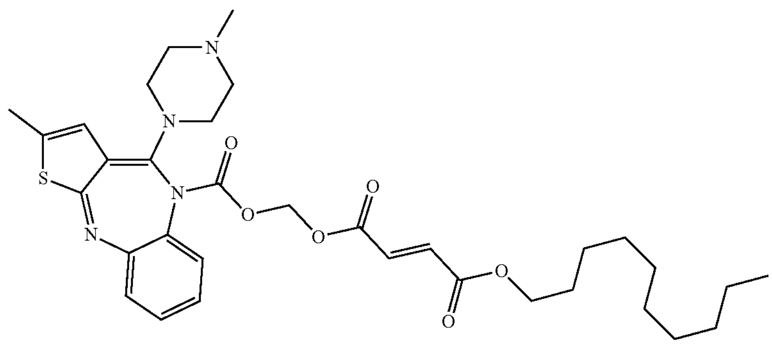 [SMILES: CCCCCCCCCCOC(=O)/C=C/C(=O)OCOC(=O)N1C(N2CCN(C)CC2)=c2cc(C)sc2=Nc2ccccc21] |
| 146. | 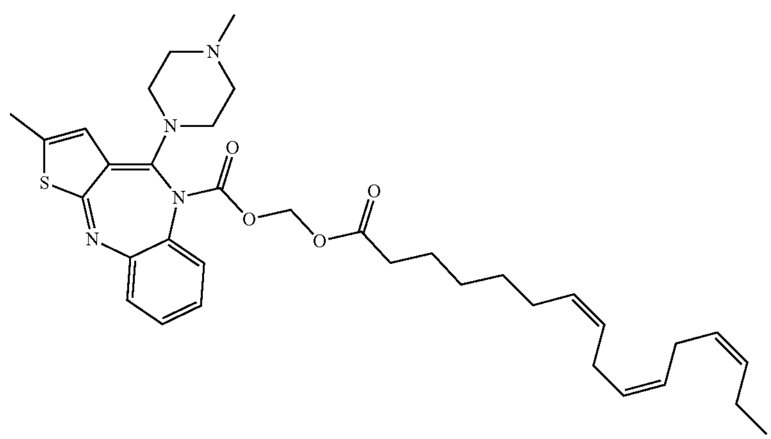 [SMILES: CC/C=C\C/C=C\C/C=C\CCCCCC(=O)OCOC(=O)N1C(N2CCN(C)CC2)=c2cc(C)sc2=Nc2ccccc21] |

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2- carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted, saturated aliphatic hydrocarbon radicals/groups having the specified number of carbons. Preferred alkyl groups comprise about 1 to about 24 carbon atoms ("$C_1$-$C_{24}$") preferably about 7 to about 24 carbon atoms ("$C_7$-$C_{24}$"), preferably about 8 to about 24 carbon atoms ("$C_8$-$C_{24}$"), preferably about 9 to about 24 carbon atoms ("$C_9$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tent-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4- thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkyl sulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound", "drug", and "prodrug" as used herein all include the compounds, drugs and prodrugs having the formulas disclosed herein. The compounds of the invention can occur in forms including pharmaceutically acceptable salts, solvates, hydrates, crystalline forms, amorphous forms, polymorphs, enantiomers, diastereoisomers, racemates and the like.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

EXAMPLES

The compositions and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the processes, formulations and/or methods of the invention may be made without departing from the spirit of the invention and the scope of the appended claims.

Synthesis of Compounds The compounds of the invention can be synthesized by the method set forth in Schemes 1A and 1B.

Scheme 1A

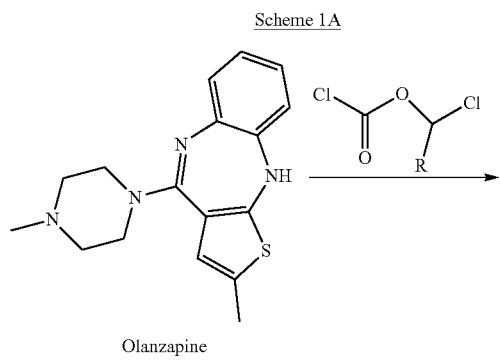

Olanzapine

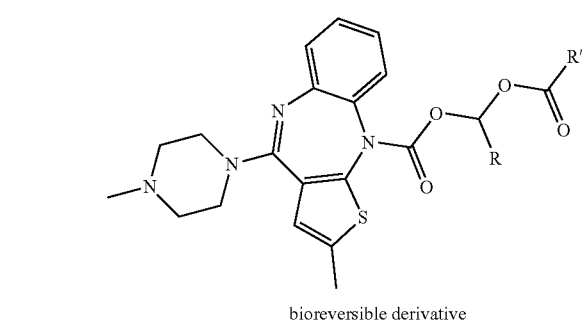

bioreversible derivative

Scheme 1B

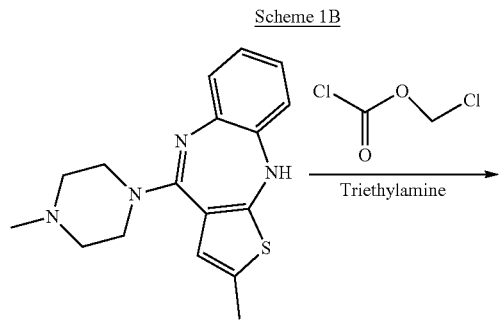

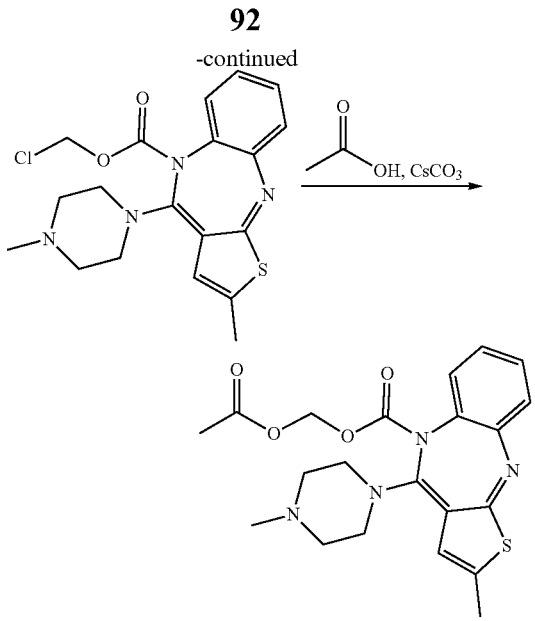

Schemes 1A and 1B illustrate the synthesis of a compound of Formula I by condensation of the parent drug compound with chloromethyl chloroformate, followed by condensation with a carboxylic acid.

Example 1

(tetradecanoyloxy)methyl 2-methyl-4-(4-methylpiperazin-1-yl)-5H-benzo[b]thieno[2,3-e][1,4]diazepine-5-carboxylate (Compound 127)

Synthesis of chloromethyl 2-methyl-4-(4-methylpiperazin-1-yl)-5H-benzo[b]thieno[2,3-e][1,4]diazepine-5-carboxylate [A]:

To a solution of olanzapine (18.0 g, 57.7 mmol) and triethylamine (16 mL, 0.12 mol) in dichloromethane (250 mL) was warmed to 35° C. and once a clear solution formed, the reaction was cooled to 5° C. To this was added chloromethyl chloroformate (7.6 mL, 86.5 mmol) over 20 minutes. The reaction was stirred at room temperature for 30 min and allowed to warm to room temperature. After 15 min at room temperature the reaction mixture was diluted with dichloromethane (100 mL), then washed with aq satd $NaHCO_3$ (75 mL) and water (350 mL). The organic phase was dried over $MgSO_4$ and filtered. The organic phase was then concentrated under vacuum at 45° C. to a volume of ~150mL. The mixture was diluted with ethyl acetate (30mL) and ~20-30mL further was evaporated under vacuum. The mixture was cooled to room temperature and the resulting solid precipitate filtered and washed with ethyl acetate. After drying under vacuum at 35° C. for 90 min chloromethyl 2-methyl-4-(4-methylpiperazin-1-yl)-5H-benzo[b]thieno[2,3-e] [1,4]diazepine-5-carboxylate [A] (17.1g, 73%) was obtained as a yellow solid.

$^1$H-NMR (300 MHz, $CDCl_3$) δ 7.62-7.14 (4H, m), 6.27-6.22 (1H, m), 5.84-5.69 (1H, m), 5.47-5.23 (1H, m), 3.89-3.63 (4H, m), 2.66-2.22 (10H, m).

General Procedure for the synthesis of aliphatic carboxylic acid substituted compounds derived from [A]:

To a solution of chloromethyl 2-methyl-4-(4-methylpiperazin-1-yl)-5H-benzo[b]thieno[2,3-e][1,4]diazepine-5-carboxylate [A](1 equiv) in dimethylformamide ((13 mL/g of [A])) was added cesium carbonate (1 equiv) and the appropriate aliphatic carboxylic acid (2 equiv). The reaction mixture was heated at 60° C. for 2-6 h, until starting material [A] had been consumed (loss of starting material determined by TLC). The reaction mixture was cooled, diluted with saturated aqueous NaHCO$_3$ (50 mL/g of [A]) and diethyl ether (75 mL/g of [A]). After being stirred for 15 min the mixture was filtered through celite and the organic phase separated. This was dried over MgSO$_4$ and evaporated. The residue was purified by column chromatography on silica eluting with 30% THF in EtOAc and the product containing fraction combined and evaporated. The residue was co-evaporated from hexanes.

Using the procedure as described above gave (tetradecanoyloxy)methyl 2-methyl-4-(4-methylpiperazin-1-yl)-5H-benzo[b]thieno[2,3 -e][1,4]diazepine-5-carboxylate, Compound 127 (1.95g, 48%) as a yellow oil.
$^1$H-NMR (300 MHz, CDCl$_3$) δ 7.63-7.54 (1H, m), 7.46-7.37 (1H, m), 7.36-7.26 (1H, m), 7.18-7.05 (1H, m), 6.28-6.19 (1H, m), 5.66-5.56 (1.5H, m), 5.38-5.34 (1H, m), 3.90-3.80 (2H, m), 3.69-3.54 (2H, m), 2.50-2.40 (4H, m), 2.32-2.25 (6H, m), 1.61-1.51 (2H, s), 1.32-1.22 (14H, m), 0.87 (3H, t). [M+H]$^+$=597.06.

Example 2

(palmitoyloxy)methyl 2-methyl-4-(4-methylpiperazin-1-yl)-5H-benzo[b]thieno[2,3-e][1,4]diazepine-5-carboxylate (Compound 56)

Using the procedure as described above for (octanoyloxy)methyl 2-methyl-4-(4-methylpiperazin-1-yl)-5H-benzo[b]thieno[2,3-e][1,4]diazepine-5-carboxylate except heated at 60° C. for 1 day gave (palmitoyloxy)methyl 2-methyl-4-(4-methylpiperazin-1-yl)-5H-benzo[b]thieno[2,3-e][1,4]diazepine-5-carboxylate Compound 56 (1.51 g, 75%) as a yellow oil.
$^1$H-NMR (300 MHz, CDCl$_3$) δ 7.62-7.55 (1H, m), 7.45-7.21 (2H, m), 7.17-7.08 (1H, m), 6.26-6.20 (1H, m), 5.66-5.35 (2H, m), 3.90-3.79 (2H, m), 3.68-3.54 (2H, m), 2.47-2.45 (4H, m), 2.33-2.24 (8H, m), 1.61-1.50 (2H, m), 1.35-1.15 (24H, m), 0.92-0.81 (3H, m).

Example 3

(stearoyloxy)methyl 2-methyl-4-(4-methylpiperazin-1-yl)-5H-benzo[b]thieno[2,3-e][1,4]diazepine-5-carboxylate (Compound 111)

Using the procedure as described above for (octanoyloxy)methyl 2-methyl-4-(4-methylpiperazin-1-yl)-5H-benzo[b]thieno[2,3-e][1,4]diazepine-5-carboxylate gave (stearoyloxy)methyl 2-methyl-4-(4-methylpiperazin-1-yl)-5H-benzo[b]thieno[2,3-e][1,4]diazepine-5-carboxylate Compound 111 (1.51 g, 75%) as a yellow oil.
$^1$H-NMR (300 MHz, CDCl$_3$) δ 7.63-7.54 (1H, m), 7.46-7.37 (1H, m), 7.36-7.26 (1H, m), 7.18-7.07 (1H, m), 6.28-6.19 (1H, m), 5.67-5.56 (1.5H, m), 5.38-5.34 (1H, m), 3.91-3.78 (2H, m), 3.69-3.54 (2H, m), 2.50-2.40 (4H, m), 2.31-2.24 (6H, m), 1.61-1.50 (2H, s), 1.34-1.20 (30H, m), 0.87 (3H, t). [M+H]$^+$=653.14.

Example 4 (icosanoyloxy)methyl 2-methyl-4-(4-methylpiperazin-1-yl)-5H-benzo[b]thieno[2,3-e][1,4]diazepine-5-carboxylate (Compound 112)

Using the procedure as described above for (octanoyloxy)methyl 2-methyl-4-(4-methylpiperazin-1-yl)-5H-benzo[b]thieno[2,3-e][1,4]diazepine-5-carboxylate gave (icosanoyloxy)methyl 2-methyl-4-(4-methylpiperazin-1-yl)-5H-benzo[b]thieno[2,3-e][1,4]diazepine-5-carboxylate Compound 112 (1.51 g, 75%) as a yellow oil.
$^1$H-NMR (300 MHz, CDCl$_3$) δ 7.63-7.54 (1H, m), 7.46-7.37 (1H, m), 7.36-7.26 (1H, m), 7.18-7.07 (1H, m), 6.28-6.19 (1H, m), 5.67-5.57 (1.5H, m), 5.37-5.34 (1H, m), 3.90-3.78 (2H, m), 3.69-3.53 (2H, m), 2.49-2.40 (4H, m), 2.32-2.24 (6H, m), 1.61-1.50 (2H, s), 1.34-1.20 (34H, m), 0.87 (3H, t). [M+H]$^+$=681.19.

Example 5 1-(palmitoyloxy)ethyl 2-methyl-4-(4-methylpiperazin-1-yl)-5H-benzo[b]thieno[2,3-e][1,4]diazepine-5-carboxylate (Compound 142)
Synthesis of chloroethyl 2-methyl-4-(4-methylpiperazin-1-yl)-5H-benzo[b]thieno[2,3-e][1,4]diazepine-5-carboxylate [B].

To a solution of olanzapine (1.70 g, 5.44 mmol) in dichloromethane (50 mL) at 0° C. was added triethylamine (1.14 mL, 8.16 mmol) followed by 1-chloroethyl chloroformate (0.70 mL, 6.53 mmol) dropwise. TLC after 3 hours indicated starting material still remaining therefore more 1-chloroethyl chloroformate (0.2 mL) was added and stirred for a further 2 hours. The reaction was diluted with dichloromethane (20 mL) and washed with aq satd NaHCO$_3$ (50 mL), dried (MgSO4) and concentrated. The crude product was purified by column chromatography on silica eluting with 2-5% MeOH/dichloromethane to give 1-chloroethyl 2-methyl-4-(4-methylpiperazin-1-yl)-5H-benzo[b]thieno[2,3-e][1,4]diazepine-5-carboxylate (1.33 g, 58% yield) as an orange foam.
$^1$H-NMR (300 MHz, CDCl$_3$) δ 7.61-7.55 (1H, m), 7.45-7.09 (3H, m), 6.41-6.21 (2H, m), 3.88-3.82 (2H, m), 3.67-3.58 (2H, m), 2.53-2.50 (4H, m), 2.32-2.29 (6H, m), 1.63-1.46 (3H, m).
General Procedure for the synthesis of aliphatic carboxylic acid substituted compounds derived from [B]:

The appropriate aliphatic carboxylic acid (1.5 equiv) and diisopropylethylamine (1.5 equiv) were premixed then added to 1-chloroethyl 2-methyl-4-(4-methylpiperazin-1-yl)-5H-benzo[b]thieno[2,3-e][1,4]diazepine-5-carboxylate [B] (1 equiv). The reaction was cooled to room temperature, diluted with diethyl ether (50 mL/g [B]), washed with aq satd NaHCO$_3$ (50 mL/g [B]), brine (50 mL/g [B]), dried (MgSO4) and concentrated. The crude product was purified by column chromatography on silica eluting with 1% triethylamine/dichloromethane then further purified using column chromatography on silica eluting with 2-4% MeOH/dichloromethane.

Using the procedure as described above gave 1-(palmitoyloxy)ethyl 2-methyl-4-(4-methylpiperazin-1-yl)-5H-benzo[b]thieno[2,3-e][1,4]diazepine-5-carboxylate, Compound 142 (1.36 g, 54%) as a yellow oil.
$^1$H-NMR (300 MHz, CDCl$_3$) δ 7.60-7.54 (1H, m), 7.43-7.03 (3H, m), 6.64-6.54 (1H, m), 6.26-6.21 (1H, m), 3.93-3.80 (2H, m), 3.76-3.55 (2H, m), 2.48-2.40 (4H, m), 2.33-2.20 (8H, m), 1.64-1.50 (2H, m), 1.35-1.16 (27H, m), 0.92-0.83 (3H, m). [M+H]$^+$=639.57.

Example 6

General procedure for the synthesis of Compounds-7-9

Synthesis of chloromethyl 2-methyl-4-(4-methylpiperazin-1-yl)-10H-benzo[b]thieno[2,3-e][1,4]diazepine-10-carboxylate [C]
To a solution of olanzapine (5.0 g, 16 mmol) in tetrahydrofuran (50 mL) at −78° C. was added tetramethylethylenediamine (2.4 mL, 16 mmol), followed by 2M n-BuLi in hexanes (8.0 mL, 16 mmol) over 5 min. The reaction mixture was stirred for 15 min and then chloromethyl chloroformate (2.1 mL, 24 mmol) added and the reaction mixture stirred a further 30 min. The reaction mixture was then warmed to room temperature, stirred for 1 h and quenched with water (50 mL). This mixture was diluted with brine (50 mL) and extracted with ethyl acetate (50 mL). The organic phase was dried over $MgSO_4$, evaporated and the residue further purified by column chromatography on silica eluting with 0.2:1:1 methanol/dichloromethane/ethyl acetate to give chloromethyl 2-methyl-4-(4-methylpiperazin-1-yl)-10H-benzo[b]thieno[2,3-e][1,4]diazepine-10-carboxylate [C] (5.6 g, ~50% pure by $^1$H NMR and LCMS). This was used directly in the next reaction without further purification.
$^1$H-NMR (300 MHz, $CDCl_3$) δ 7.02-7.30 (4H, m), 6.45 (1H, s), 5.78-5.92 (1.5H, m), 5.52-5.60 (0.5H, m), 3.50-3.70 (4H, m), 2.35-2.55 (7H, m), 2.32 (3H, s). $[M+H]^+$=405.0.

General Procedure for the synthesis of aliphatic carboxylic acid substituted compounds derived from [C]:

To a solution of chloromethyl 2-methyl-4-(4-methylpiperazin-1-yl)-10H-benzo[b]thieno[2,3-e][1,4]diazepine-10-carboxylate (C:1 equiv) in dimethylformamide (13 mL/g of [C]) was added $Cs_2CO_3$ (1 equiv) and the appropriate aliphatic carboxylic acid (2 equiv). The reaction mixture was heated at 65° C. for 2-6 h, until starting material [A] had been consumed (loss of starting material determined by TLC). The reaction mixture was cooled, diluted with saturated aqueous NaHCO3 (50 mL/g of [C]) and ethyl acetate (75 mL/g of [C]). After being stirred for 15 min the mixture was filtered through celite and the organic phase separated. This was dried over $MgSO_4$ and evaporated. The residue was further purified by column chromatography on silica eluting with 1:9 methanol/ethyl acetate and after evaporation of the product containing fractions, the residue was co-evaporated with hexane (2×10 mL/g [C]).

Example 7

(tetradecanoyloxy)methyl 2-methyl-4-(4-methylpiperazin-1-yl)-10H-benzo[b]thieno[2,3-e][1,4]diazepine-10-carboxylate (Compound 6)

Using the general procedure described in Example 6 above employing tetradecanoic acid and 2.8g of the intermediate [A], provided (tetradecanoyloxy)methyl 2-methyl-4-(4-methylpiperazin-1-yl)-10H-benzo[b]thieno[2,3-e][1,4]diazepine-10-carboxylate (Compound 7) (1.60 g, 39% yield) as a pale yellow oil.
$^1$H-NMR (300 MHz, $CDCl_3$) δ 7.00-7.25 (4H, m), 6.43 (1H, s), 5.62-5.90 (2H, m), 3.51-3.65 (4H, m), 2.30-2.56 (10H, m), 1.58-1.66 (2H, m), 1.20-1.34 (22H), 0.87 (3H, t). $[M+H]^+$=597.12.

Example 8

(hexadecanoyloxy)methyl 2-methyl-4-(4-methylpiperazin-1-yl)-10H-benzo[b]thieno[2,3-e][1,4]diazepine-10-carboxylate (Compound 7)

Using the general procedure described in Example 6 above employing palmitic acid and 1.0 g of the intermediate [A], provided (hexadecanoyloxy)methyl 2-methyl-4-(4-methylpiperazin-1-yl)-10H-benzo[b]thieno[2,3-e][1,4]diazepine-10-carboxylate (Compound 8) (1.60 g, 39% yield) as a pale yellow oil.
$^1$H-NMR (300 MHz, $CDCl_3$) δ 7.00-7.25 (4H, m), 6.43 (1H, s), 5.62-5.90 (2H, m), 3.51-3.66 (4H, m), 2.30-2.56 (10H, m), 1.58-1.68 (2H, m), 1.20-1.34 (26H), 0.87 (3H, t). $[M+H]^+$=625.07.

Example 9

(stearoyloxy)methyl 2-methyl-4-(4-methylpiperazin-1-yl)-10H-benzo[b]thieno[2,3-e][1,4]diazepine-10-carboxylate (Compound 8)

Using the general procedure described in Example 6 above employing stearic acid and 2.8 g of the intermediate [A], provided (stearoyloxy)methyl 2-methyl-4-(4-methylpiperazin-1-yl)-10H-benzo[b]thieno[2,3-e][1,4]diazepine-10-carboxylate (Compound-9) (1.44 g, 32% yield) as a pale yellow oil.
$^1$H-NMR (300 MHz, $CDCl_3$) δ 6.99-7.22 (4H, m), 6.43 (1H, s), 5.62-5.88 (2H, m), 3.51-3.66 (4H, m), 2.30-2.66 (10H, m), 1.55-1.70 (2H, m), 1.20-1.34 (30H), 0.87 (3H, t). $[M+H]^+$=653.21.

Example 10

Pharmacokinetic Evaluation of Prodrugs in Rats

Animals

Male Sprague-Dawley rats (Charles River Laboratories, Wilmington, Mass.) 25 male Sprague-Dawley rats are obtained. Approximately 24 rats are used in each study. Rats are approximately 325-350 g at time of arrival, and are housed 2 per cage with ad libitum chow and water. Environmental conditions in the housing room are 64-76° F., 30% to 70% relative humidity, and 12:12-h light:dark cycle. All experiments are approved by the Institutional Animal Care and Use Committee.

Test Compounds

Prodrug compounds (Compound 56, Compound 111, and Compound 112) of the invention and corresponding parent drugs of the prodrugs are tested.

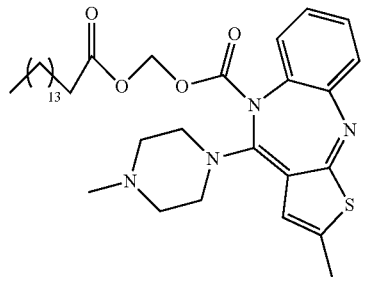

Compound 56

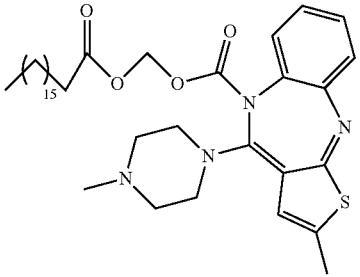

Compound 111

Compound 112

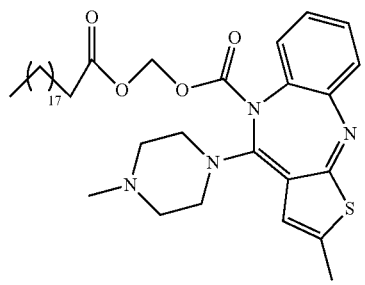

Compound 111

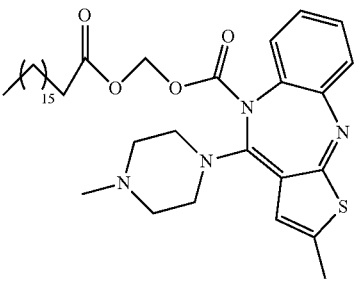

Compound 112

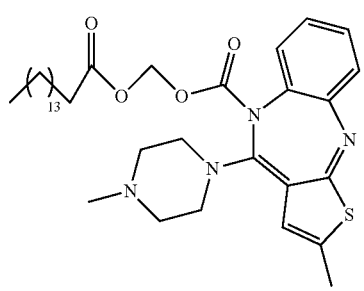

Pharmacokinetics Study

Animals

Male Sprague-Dawley rats (Charles River Laboratories, Wilmington, Mass.) 25 male Sprague-Dawley rats are obtained. Approximately 24 rats are used in each study. Rats are approximately 325-350 g at time of arrival, and are housed 2 per cage with ad libitum chow and water. Environmental conditions in the housing room are 64-76° F., 30% to 70% relative humidity, and 12:12-h light:dark cycle. All experiments are approved by the Institutional Animal Care and Use Committee.

Test Compounds

Prodrug compounds (Compound 56, Compound 111 and Compound 112) of the invention and corresponding parent drugs of the prodrugs are tested.

Compound 56

Pharmacokinetics Study

Rats are dosed IM by means of a 25 gauge, ⅝ in. needle with 1 cc syringe. 0.3mL suspension is withdrawn from the vial containing the test compound. The rat is injected in the muscles of the hind limb after anesthesia with isoflourane. Blood samples are collected via a lateral tail vein after brief anesthesia with Isoflurane. A 27½ G needle and 1cc syringe without an anticoagulant is used for the blood collection. Approximately 250 µL of whole blood is collected at each sampling time point of 1 hour, 6 hours, 24 hours and 2, 3, 6, 7, 10, 14 days after administration. Once collected, whole blood is immediately transferred to tubes containing an esterase inhibitor and anti-coagulant, inverted 10-15 times and immediately placed on ice. The tubes are centrifuged for 2 minutes at >14,000 g's (11500 RPMs using Eppendorf Centrifuge at 2-6° C. to separate plasma. Plasma samples are transferred to labeled plain tubes and stored frozen at <−70° C. The study design is shown in Table 5 and the PK results are given in Table 6.

TABLE 5

| Compound | Vehicle | Group | # of Animals | Dose (mg) | Active Conc. (mg/mL) | Dose Volume (mL) | Route |
|---|---|---|---|---|---|---|---|
| Relprevv | Zyprexa | A | 3 | 3 | 10 | 0.3 | IM |
| Compound 56 | CMC Vehicle (2% CMC, 0.2% Tween 20 in 10 mM PBS pH 6.8,) | C | 6 | 3 | 10 | 0.3 | IM |
| Compound 111 | CMC Vehicle (2% CMC, 0.2% Tween 20 in 10 mM PBS pH 6.8,) | D | 6 | 3 | 10 | 0.3 | IM |
| Compound 112 | CMC Vehicle (2% CMC, 0.2% Tween 20 in 10 mM PBS pH 6.8,) | E | 6 | 3 | 10 | 0.3 | IM |

Data Analysis

The Olanzapine and prodrug concentrations in plasma samples were analyzed by liquid chromatography-tandem mass spectroscopy using appropriate parameters for each compound.

Half life, maximal concentration, and AUC are calculated using WinNonlin software, version 5.2 (Pharsight, St. Louis, Mo.). (FIGS. 1-4).

TABLE 6

| Compound | OLZ $AUC_{INF}$ (hr*ng/mL) | OLZ $T_{max}$ (hr) | OLZ $C_{max}$ (ng/mL) | OLZ $T_{last}^x$ (hr) | Relative exposure of prodrug$^y$ |
|---|---|---|---|---|---|
| Relprevv | 1535 | 6 | 63.2 | 168 | — |
| Compound 56 | 1791 | 48 | 16.6 | >336 | Not detected |
| Compound 111 | 2170 | 48 | 13.6 | >336 | <3% |
| Compound 112 | 1293 | 148 | 6.0 | >336 | 12% |

$^t$ This concentration was extrapolated above the upper limit of quantification (100 ng/mL).
$^x$ The last time point with a measured concentration above the lower limit of quantitation.
$^y$ Calculated using the formula: ([Prodrug AUC$_{last}$/(MW$_{prodrug}$)]/[OLZ AUC$_{INF}$/(MW$_{OLZ}$)]) * 100

Conclusions:

Three of the compounds (56, 111, and 112) provided sustained release concentrations of Olanzapine for at least 14 days, with delayed $T_{max}$ and $T_{last}$, and lower $C_{max}$ relative to the current commercial extended release injectable, Relprevv (Olanzapine Pamoate salt). The slow absorption of these compounds is illustrated by the delayed Olanzapine $T_{max}$. All of the compounds efficiently deliver Olanzapine, providing exposures of Olanzapine that are comparable to the measured Olanzapine exposure delivered by Relprevv. In addition, the relative exposure of the prodrugs as compared on a molar basis to that of Olanzapine is low in all cases.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed is:

1. A method for sustained delivery of a secondary amine-containing parent drug to a patient comprising administering a compound of Formula I:

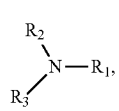

Formula I wherein:
$R_1$ is —C(O)OCH$_2$OC(O)R$_6$;
$R_6$ is selected from $C_{13}$-$C_{26}$-alkyl, substituted $C_{13}$-$C_{26}$-alkyl, $C_{13}$-$C_{26}$-alkenyl, substituted $C_{13}$-$C_{26}$-alkenyl, $C_{13}$-$C_{26}$-alkynyl, substituted $C_{13}$-$C_{26}$-alkynl, $C_{13}$-$C_{26}$-cycloalkyl, substituted $C_{13}$-$C_{26}$-cycloalkyl, aryl-$C_{13}$-$C_{26}$-alkyl, substituted aryl-$C_{13}$-$C_{26}$-alkyl, $C_1$-$C_{10}$-aryl, substituted $C_1$-$C_{10}$-aryl, heteroaryl-$C_{13}$-$C_{26}$-alkyl, substituted heteroaryl-$C_{13}$-$C_{26}$-alkyl; optionally substituted $C_{13}$-$C_{26}$-alkylaryl, optionally substituted $C_{13}$-$C_{26}$-alkenylaryl and optionally substituted $C_{13}$-$C_{26}$-alkynylaryl; and $R_2$ and $R_3$, together with the nitrogen atom to which they are attached, form a secondary amine-containing parent drug, or a substituted secondary amine-containing parent drug.

2. The method according to claim 1, wherein upon administration of a compound of Formula I to the patient, release of the parent drug from the prodrug is sustained release.

3. The method according to claim 1, wherein the compound of Formula I further comprises a biocompatible delivery system for delivering the prodrug wherein the system is capable of minimizing accelerated hydrolytic cleavage of the prodrug by minimizing exposure of the prodrug to water.

4. The method according to claim 1, wherein the parent drug is present in the blood stream of the patient for a period selected from at least 12 hours, at least 24 hours, at least 36 hours, at least 48 hours, at least 4 days, at least one week, at least one month and at least 3 months.

5. The method according to claim 1, wherein the administering step is by injection or oral delivery.

6. The method according to claim 1, wherein said parent drug is selected from atenolol, atomoxetine, clozapine, desipramine, desloratadine (clarinex), diclofenac, doripenem, duloxetine, enalapril, ertapenem, fluoxetine, metoprolol, mecamylamine, meropenem, methylphenidate, dtmp (dextrorotary methylphenidate), olanzapine, paroxetine, pramipexole, rasagiline, (r)-rasagiline, salbutamol/albuterol, tamsulosin, varenicline (chantix), and vildagliptin.

7. The method according to claim 1, wherein said parent drug is alprenolol, acebutolol, amidephrine, amineptine, amosulalol, amoxapine, amphetaminil, atenolol, atomoxetine, balofloxacin, bamethan, befunolol, benazepril, benfluorex, benzoctamine, betahistine, betaxolol, bevantolol, bifemelane, bisoprolol, brinzolamide, bufeniode, butethamine, camylofine, carazolol, carticaine, carvedilol, cephaeline, ciprofloxacin, clozapine, clobenzorex, clorprenaline, cyclopentamine, delapril, demexiptiline, denopamine, desipramine, desloratadine (clarinex), diclofenac, dimetofrine, dioxadrol, dobutamine, dopexamine, doripenem, dorzolamide, droprenilamine, duloxetine, eltoprazine, enalapril, enoxacin, epinephrine, ertapenem, esaprazole, esmolol, etoxadrol, fasudil, fendiline, fenethylline, fenfluramine, fenoldopam, fenoterol, fenproporex, flecainide, fluoxetine, formoterol, frovatriptan, gaboxadol, garenoxacin, gatifloxacin, grepafloxacin, hexoprenaline, imidapril, indalpine, indecainide, indeloxazine hydrochloride, isoxsuprine, ispronicline, labetalol, landiolol, lapatinib, levophacetoperane, lisinopril, lomefloxacin, lotrafiban, maprotiline, mecamylamine, mefloquine, mepindolol, meropenem, metapramine, metaproterenol, methoxyphenamine, dtmp (dextrorotary methylphenidate), methylphenidate, metipranolol, metoprolol, mitoxantrone, mivazerol, moexipril, moprolol, moxifloxacin, nebivolol, nifenalol, nipradilol, norfloxacin, nortriptyline, nylidrin, olanzapine, oxamniquine, oxprenolol, oxyfedrine, paroxetine, perhexiline, phenmetrazine, phenylephrine, phenylpropylmethylamine, pholedrine, picilorex, pimefylline, pindolol, pipemidic acid, piridocaine, practolol, pradofloxacin, pramipexole, pramiverin, prenalterol, prenylamine, prilocaine, procaterol, pronethalol, propafenone, propranolol, propylhexedrine, protokylol, protriptyline, pseudoephedrine, reboxetine, rasagiline, (r)-rasagiline, repinotan, reproterol, rimiterol, ritodrine, safinamide, salbutamol/albuterol, salmeterol, sarizotan, sertraline, silodosin, sotalol, soterenol, sparfloxacin, spirapril, sulfinalol, synephrine, tamsulosin, tebanicline, tianeptine, tirofiban, tretoquinol, trimetazidine, troxipide, varenicline (champix), vildagliptin, viloxazine, viquidil and xamoterol.
8. The method according to claim 1, wherein the compound of Formula I is selected from:
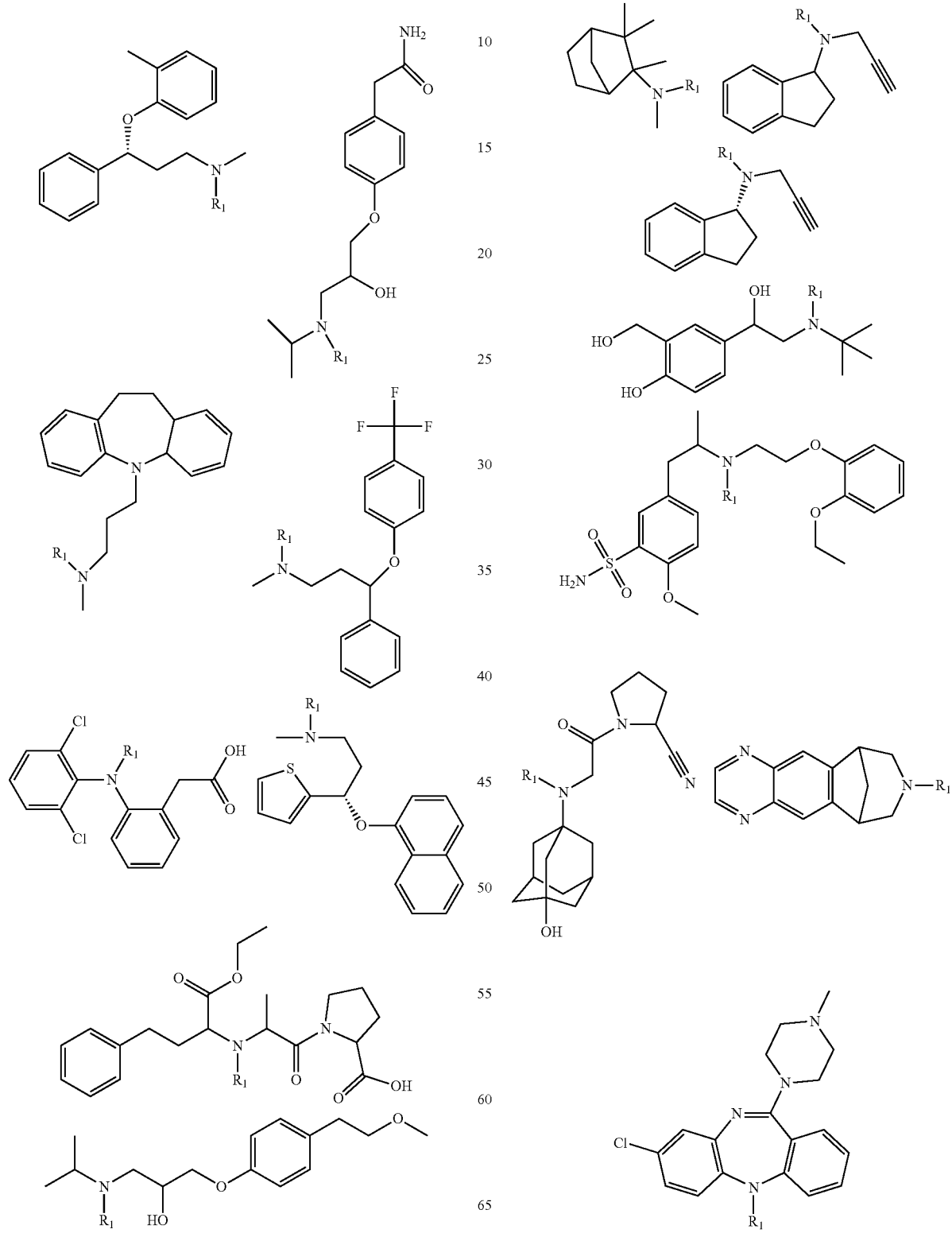

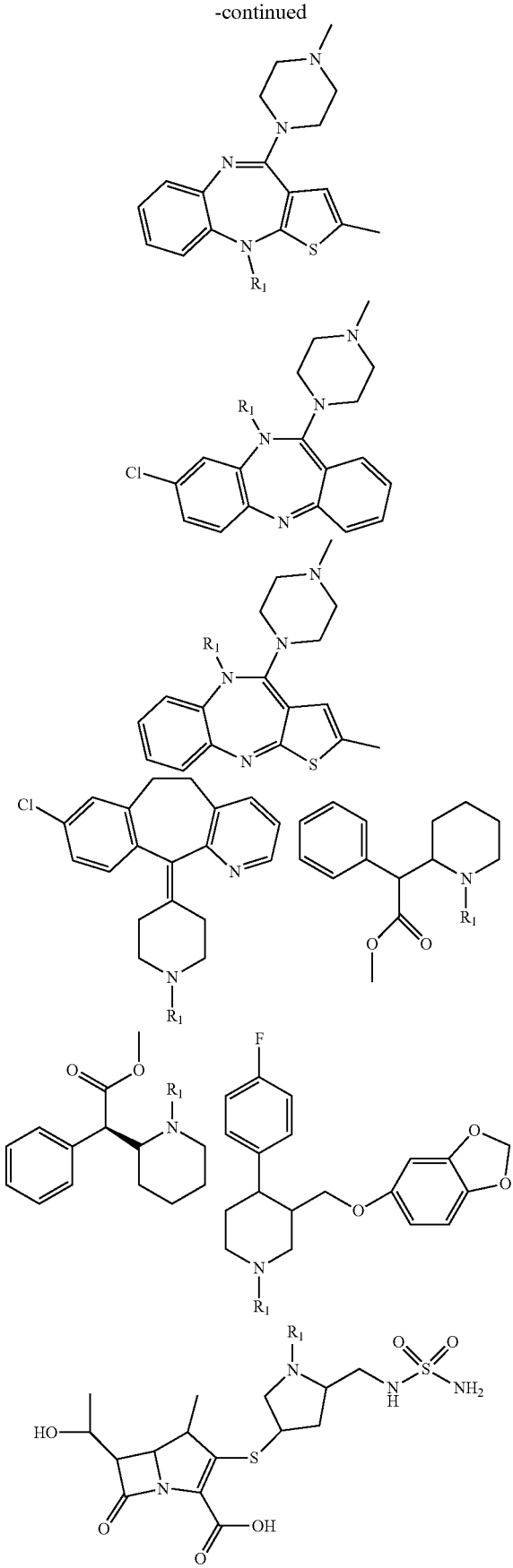

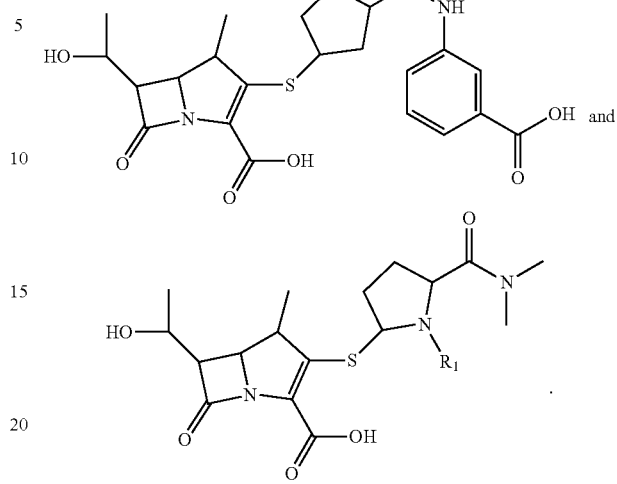

9. The method according to claim 1, wherein R6 is selected from $C_{13}$-$C_{25}$-alkyl, substituted $C_{13}$-$C_{25}$-alkyl, $C_{13}$-$C_{25}$-alkenyl, substituted $C_{13}$-$C_{25}$-alkenyl, $C_{13}$-$C_{25}$-alkynyl, substituted $C_{13}$-$C_{25}$-alkynyl, $C_{13}$-$C_{25}$-cycloalkyl, and substituted $C_{13}$-$C_{25}$-cycloalkyl.

10. The method according to claim 1, wherein $R_6$ is selected from $C_{17}$-$C_{21}$-alkyl, substituted $C_{17}$-$C_{21}$-alkyl, $C_{17}$-$C_{21}$-alkenyl, substituted $C_{17}$-$C_{21}$-alkenyl, $C_{17}$-$C_{21}$-alkynyl, substituted $C_{17}$-$C_{21}$-alkynyl, $C_{17}$-$C_{21}$-cycloalkyl, and substituted $C_{17}$-$C_{21}$-cycloalkyl.

11. The method according to claim 1, wherein $R_6$ is selected from $C_{17}$-alkyl, substituted $C_{17}$-alkyl, $C_{17}$-alkenyl, substituted-$C_{17}$-alkenyl, $C_{17}$-alkynyl, substituted $C_{17}$-alkynyl, $C_{17}$-cycloalkyl, and substituted $C_{17}$-cycloalkyl.

12. The method according to claim 1, wherein $R_6$ is selected from $C_{19}$-alkyl, substituted $C_{19}$-alkyl, $C_{19}$-alkenyl, substituted $C_{19}$-alkenyl, $C_{19}$-alkynyl, substituted $C_{19}$-alkynyl, $C_{19}$-cycloalkyl, and substituted $C_{19}$-cycloalkyl.

13. The method according to claim 1, wherein $R_1$ is selected from

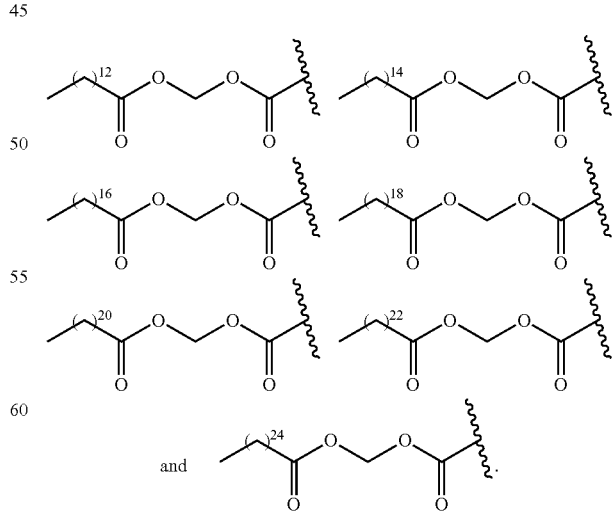

14. The method according to claim 1, wherein the compound of Formula I is selected:

| Compound # | Structure | Compound # | Structure |
|---|---|---|---|
| 10. | 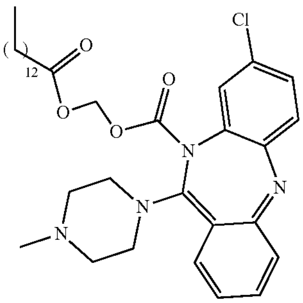 | 62. | 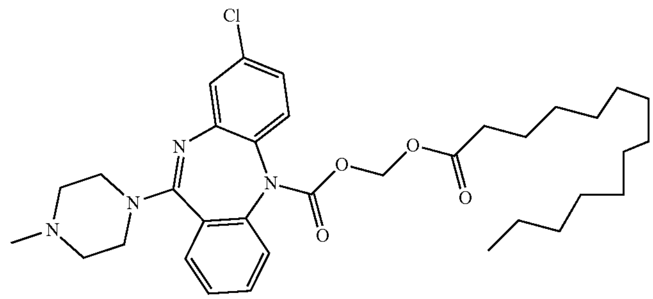 [SMILES: CCCCCCCCCCCCCC(=O)OCOC(=O)N1c2ccc(Cl)cc2N=C(N2CCN(C)CC2)c2ccccc21] |
| 11. | 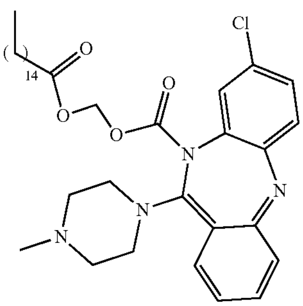 | 63. | 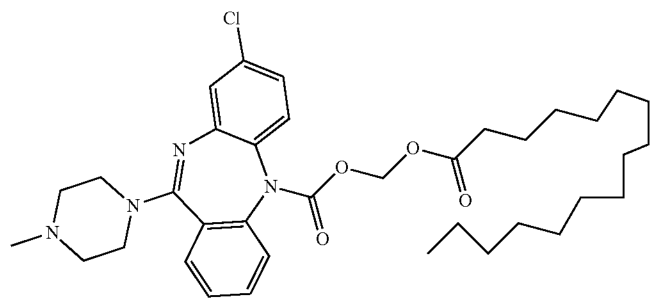 [SMILES: CCCCCCCCCCCCCCCC(=O)OCOC(=O)N1c2ccc(Cl)cc2N=C(N2CCN(C)CC2)c2ccccc21] |
| 12. | 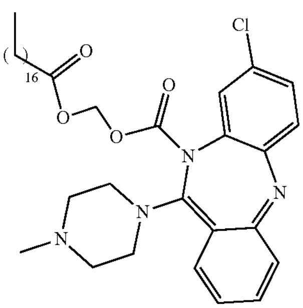 | 64. | 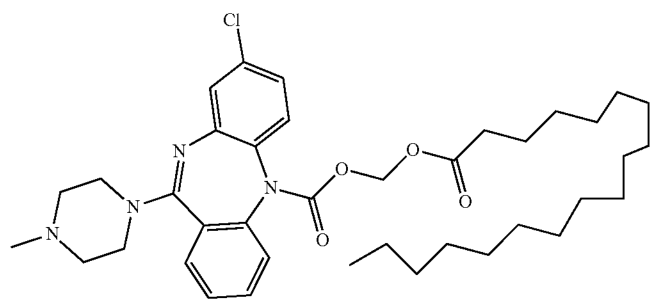 [SMILES: CCCCCCCCCCCCCCCCCC(=O)OCOC(=O)N1c2ccc(Cl)cc2N=C(N2CCN(C)CC2)c2ccccc21] |
| 13. | 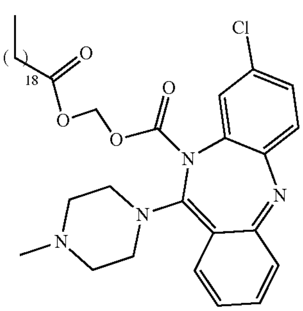 | 65. | 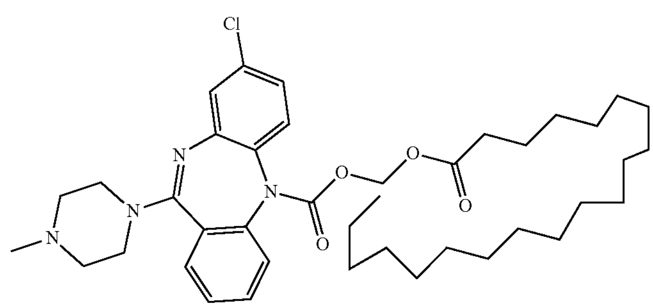 [SMILES: CCCCCCCCCCCCCCCCCCCC(=O)OCOC(=O)N1c2ccc(Cl)cc2N=C(N2CCN(C)CC2)c2ccccc21] |
| 14. | 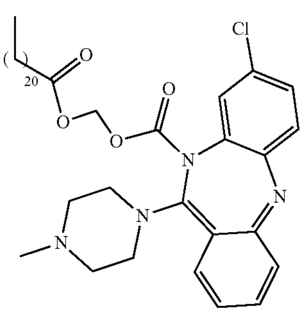 | 66. | 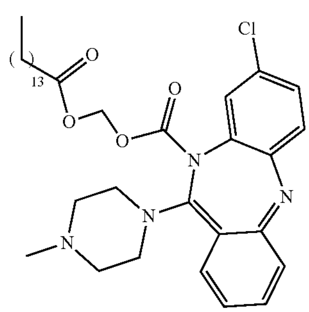 |

-continued

| Compound # | Structure | Compound # | Structure |
|---|---|---|---|
| 67. | 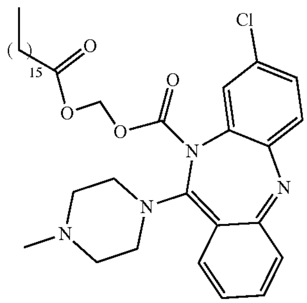 | 68. | 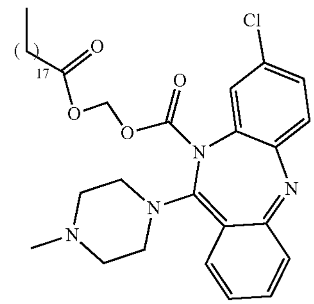 |
| 69. | 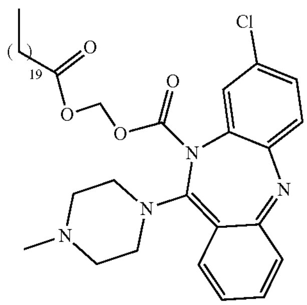 | 70. | 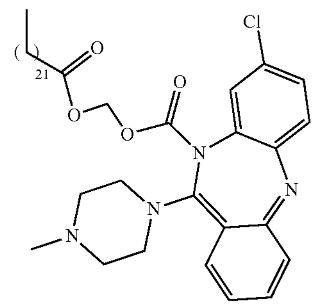 |
| 28. | 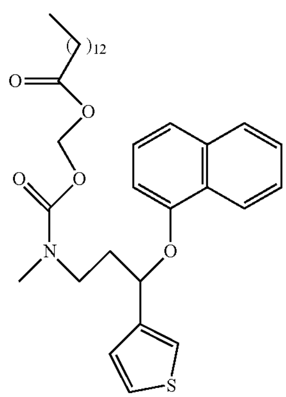 | 29. | 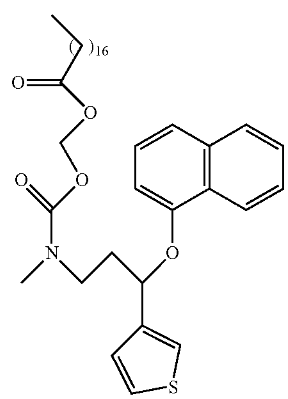 |
| 30. | 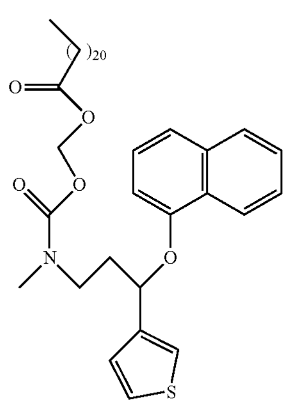 | 37. | 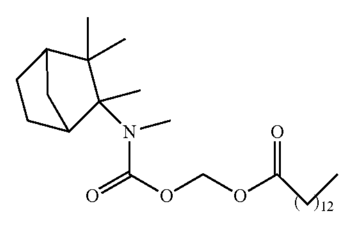 |

-continued
| Compound # | Structure | Compound # | Structure |
|---|---|---|---|
| 38. | 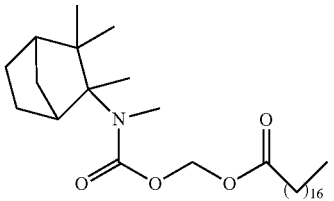 | 39. | 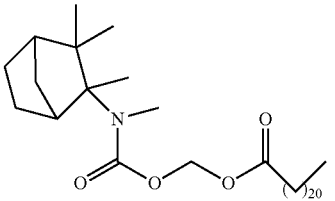 |
| 43. | 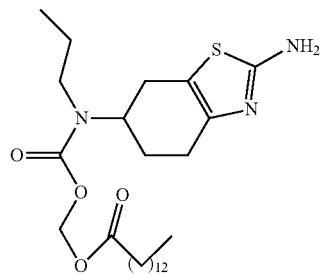 | 84. | 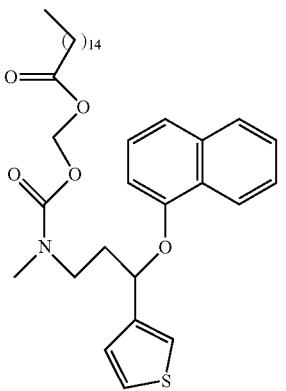 |
| 44. | 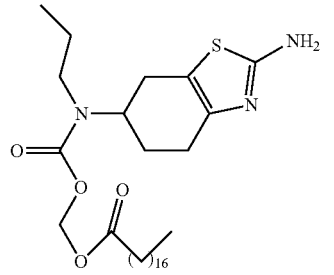 | 85. | 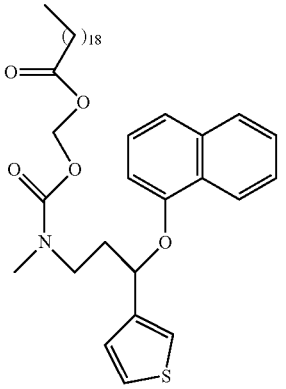 |
| 45. | 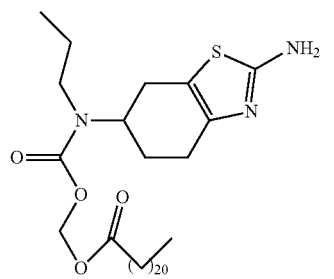 | 86. | 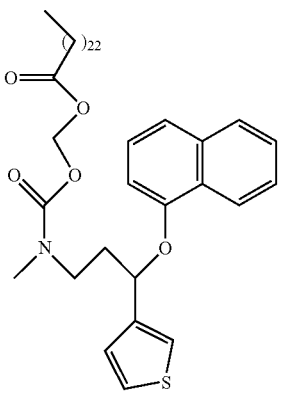 |

-continued

| Compound # | Structure | Compound # | Structure |
|---|---|---|---|
| 49. | (structure) | 50. | (structure) |
| 51. | (structure) | 93. | (structure) |
| 94. | (structure) | 95. | (structure) |
| 100. | (structure) | 99. | (structure) |
| 101. | (structure) | 105. | (structure) |
| 106. | (structure) | 107. | (structure) |

15. The method of claim 1, wherein $R_6$ is selected from $C_{15}$-$C_{23}$-alkyl, substituted $C_{15}$-$C_{23}$-alkyl, $C_{15}$-$C_{23}$-alkenyl, substituted $C_{15}$-$C_{23}$-alkenyl, $C_{15}$-$C_{23}$-alkynyl, substituted $C_{15}$-$C_{23}$-alkynyl, $C_{15}$-$C_{23}$-cycloalkyl, and substituted $C_{15}$-$C_{23}$-cycloalkyl.

* * * * *